(12) United States Patent
Kijanka et al.

(10) Patent No.: US 8,426,140 B2
(45) Date of Patent: Apr. 23, 2013

(54) METHOD OF ASSESSING COLORECTAL CANCER STATUS IN AN INDIVIDUAL

(75) Inventors: Gregor Kijanka, Dublin (IE); Dermot Kenny, Dublin (IE); Elaine Kay, Dublin (IE)

(73) Assignee: Royal College of Surgeons in Ireland, Dublin (IE)

( * ) Notice: Subject to any disclaimer, the term of this patent is extended or adjusted under 35 U.S.C. 154(b) by 0 days.

(21) Appl. No.: 12/677,898

(22) PCT Filed: Sep. 26, 2008

(86) PCT No.: PCT/IE2008/000092
§ 371 (c)(1), (2), (4) Date: Apr. 27, 2010

(87) PCT Pub. No.: WO2009/040782
PCT Pub. Date: Apr. 2, 2009

(65) Prior Publication Data
US 2010/0304410 A1 Dec. 2, 2010

Related U.S. Application Data

(60) Provisional application No. 60/995,915, filed on Sep. 28, 2007.

(51) Int. Cl.
*G01N 33/53* (2006.01)
*G01N 33/574* (2006.01)
*C12Q 1/00* (2006.01)
*C12Q 1/68* (2006.01)

(52) U.S. Cl.
USPC .............. 435/7.1; 435/4; 435/6.14; 435/7.23

(58) Field of Classification Search .................. 435/6.12, 435/6.14, 7.92
See application file for complete search history.

(56) References Cited

U.S. PATENT DOCUMENTS

2003/0219777 A1   11/2003   Shang et al.
2003/0232399 A1*  12/2003   Robertson et al. ........... 435/7.23
2006/0019256 A1*  1/2006    Clarke et al. ..................... 435/6

FOREIGN PATENT DOCUMENTS

WO   02/90986 A   11/2002

OTHER PUBLICATIONS

Tockman et al. (Cancer Res., 1992, 52:2711s-2718s).*
Pritzker (Clinical Chemistry, 2002, 48:1147-1150).*
Boon and Old ("Cancer Tumor antigens," Curr. Opin. Immunol. 9:681 1997).*
Bussow, K. et al., Genomics, 65(1):1-8 (2000). "A Human cDNA Library for High-Throughput Protein Expression Screening."
Database WPI Week 200566, AN 2005-640540, XP002512136, Shanghai Human Genome Res. Cent. (2005).
Lechpammer, M. et al., International Journal of Colorectal Disease, 19(2):114-120 (2004). "Humoral immune response to p53 correlates with clinical course in colorectal cancer patients during adjuvant chemotherapy."
Nozoe, T. et al., Hepato-Gastroenterology, 54(77):1422-1425 (2007). "Clinicopathologic significance in serum presence of anti-p53 antibody in patients with colorectal carcinoma."
Zhang, J-Y. et al., Cancer Epidemiology, 12(2):136-143 (2003). "Enhancement of antibody detection in cancer using panel of recombinant tumor-associated antigens."

* cited by examiner

*Primary Examiner* — Misook Yu
*Assistant Examiner* — Yan Xiao
(74) *Attorney, Agent, or Firm* — Nixon Peabody LLP; David S. Resnick; Leena H. Karttunen Contarino

(57) ABSTRACT

The invention relates to a method of screening a patient to identify and quantify risk of colorectal cancer, and thereby identify patients suitable for further invasive investigation such as a colonoscopy. The method employs auto-antibodies that are shown to correlate with colorectal cancer risk method and involves of assaying a biological sample from the individual for a combination of a plurality of biomarkers selected from SEQUENCE ID NO's: 1 to 12, where the combination of biomarkers is chosen such that detection of all biomarkers in the patient correlates to at least a 50% risk of the patient being positive for colorectal cancer. Detection of all of the combination of biomarkers indicates that the patient should undergo a colonoscopy. Kits for performing the method of the invention are also provided.

9 Claims, 6 Drawing Sheets

SEQUENCE LISTING

<160> NUMBER OF SEQ ID NOS: 23

<210> SEQ ID NO 1
<211> LENGTH: 742
<212> TYPE: PRT
<213> ORGANISM: Homo sapiens
<300> PUBLICATION INFORMATION:
<308> DATABASE ACCESSION NUMBER: SWISS-PROT/Q9H0M5
<309> DATABASE ENTRY DATE: 2006-05-02
<313> RELEVANT RESIDUES IN SEQ ID NO: (1)..(742)

<400> SEQUENCE: 1

```
Met Pro Cys Cys Ser His Arg Ser Cys Arg Glu Asp Pro Gly Thr Ser
1               5                   10                  15

Glu Ser Arg Glu Met Asp Pro Val Ala Phe Glu Asp Val Ala Val Asn
            20                  25                  30

Phe Thr Gln Glu Glu Trp Thr Leu Leu Asp Ile Ser Gln Lys Asn Leu
        35                  40                  45

Phe Arg Glu Val Met Leu Glu Thr Phe Arg Asn Leu Thr Ser Ile Gly
    50                  55                  60

Lys Lys Trp Ser Asp Gln Asn Ile Glu Tyr Glu Tyr Gln Asn Pro Arg
65                  70                  75                  80

Arg Ser Phe Arg Ser Leu Ile Glu Glu Lys Val Asn Glu Ile Lys Glu
                85                  90                  95

Asp Ser His Cys Gly Glu Thr Phe Thr Gln Val Pro Asp Asp Arg Leu
            100                 105                 110

Asn Phe Gln Glu Lys Lys Ala Ser Pro Glu Val Lys Ser Cys Asp Ser
        115                 120                 125

Phe Val Cys Ala Glu Val Gly Ile Gly Asn Ser Ser Phe Asn Met Ser
    130                 135                 140

Ile Arg Gly Asp Thr Gly His Lys Ala Tyr Glu Tyr Gln Glu Tyr Gly
145                 150                 155                 160

Pro Lys Pro Tyr Lys Cys Gln Gln Pro Lys Asn Lys Lys Ala Phe Arg
                165                 170                 175

Tyr Arg Pro Ser Ile Arg Thr Gln Glu Arg Asp His Thr Gly Glu Lys
            180                 185                 190

Pro Tyr Ala Cys Lys Val Cys Gly Lys Thr Phe Ile Phe His Ser Ser
        195                 200                 205

Ile Arg Arg His Met Val Met His Ser Gly Asp Gly Thr Tyr Lys Cys
    210                 215                 220

Lys Phe Cys Gly Lys Ala Phe His Ser Phe Ser Leu Tyr Leu Ile His
225                 230                 235                 240

Glu Arg Thr His Thr Gly Glu Lys Pro Tyr Glu Cys Lys Gln Cys Gly
                245                 250                 255

Lys Ser Phe Thr Tyr Ser Ala Thr Leu Gln Ile His Glu Arg Thr His
            260                 265                 270

Thr Gly Glu Lys Pro Tyr Glu Cys Ser Lys Cys Asp Lys Ala Phe His
        275                 280                 285

Ser Ser Ser Ser Tyr His Arg His Glu Arg Ser His Met Gly Glu Lys
    290                 295                 300

Pro Tyr Gln Cys Lys Glu Cys Gly Lys Ala Phe Ala Tyr Thr Ser Ser
305                 310                 315                 320

Leu Arg Arg His Glu Arg Thr His Ser Gly Lys Lys Pro Tyr Glu Cys
                325                 330                 335

Lys Gln Tyr Gly Glu Gly Leu Ser Tyr Leu Ile Ser Phe Gln Thr His
```

```
                        340             345                 350
Ile Arg Met Asn Ser Gly Glu Arg Pro Tyr Lys Cys Lys Ile Cys Gly
            355                 360                 365
Lys Gly Phe Tyr Ser Ala Lys Ser Phe Gln Thr His Glu Lys Thr His
            370                 375                 380
Thr Gly Glu Lys Arg Tyr Lys Cys Lys Gln Cys Gly Lys Ala Phe Asn
385                 390                 395                 400
Leu Ser Ser Ser Phe Arg Tyr His Glu Arg Ile His Thr Gly Glu Lys
                405                 410                 415
Pro Tyr Glu Cys Lys Gln Cys Gly Lys Ala Phe Arg Ser Ala Ser Gln
            420                 425                 430
Leu Arg Val His Gly Gly Thr His Thr Gly Glu Lys Pro Tyr Glu Cys
            435                 440                 445
Lys Glu Cys Gly Lys Ala Phe Arg Ser Thr Ser His Leu Arg Val His
            450                 455                 460
Gly Arg Thr His Thr Gly Glu Lys Pro Tyr Glu Cys Lys Glu Cys Gly
465                 470                 475                 480
Lys Ala Phe Arg Tyr Val Lys His Leu Gln Ile His Glu Arg Thr Glu
                485                 490                 495
Lys His Ile Arg Met Pro Ser Gly Glu Arg Pro Tyr Lys Cys Ser Ile
            500                 505                 510
Cys Glu Lys Gly Phe Tyr Ser Ala Lys Ser Phe Gln Thr His Glu Lys
            515                 520                 525
Thr His Thr Gly Glu Lys Pro Tyr Glu Cys Asn Gln Cys Gly Lys Ala
            530                 535                 540
Phe Arg Cys Cys Asn Ser Leu Arg Tyr His Glu Arg Thr His Thr Gly
545                 550                 555                 560
Glu Lys Pro Tyr Glu Cys Lys Gln Cys Gly Lys Ala Phe Arg Ser Ala
                565                 570                 575
Ser His Leu Arg Met His Glu Arg Thr His Thr Gly Glu Lys Pro Tyr
            580                 585                 590
Glu Cys Lys Gln Cys Gly Lys Ala Phe Ser Cys Ala Ser Asn Leu Arg
            595                 600                 605
Lys His Gly Arg Thr His Thr Gly Glu Lys Pro Tyr Glu Cys Lys Gln
            610                 615                 620
Cys Gly Lys Ala Phe Arg Ser Ala Ser Asn Leu Gln Met His Glu Arg
625                 630                 635                 640
Thr His Thr Gly Glu Lys Pro Tyr Glu Cys Lys Glu Cys Glu Lys Ala
                645                 650                 655
Phe Cys Lys Phe Ser Ser Phe Gln Ile His Glu Arg Lys His Arg Gly
            660                 665                 670
Glu Lys Pro Tyr Glu Cys Lys His Cys Gly Asn Gly Phe Thr Ser Ala
            675                 680                 685
Lys Ile Leu Gln Ile His Ala Arg Thr His Ile Gly Glu Lys His Tyr
            690                 695                 700
Glu Cys Lys Glu Cys Gly Lys Ala Phe Asn Tyr Phe Ser Ser Leu His
705                 710                 715                 720
Ile His Ala Arg Thr His Met Gly Glu Lys Pro Tyr Glu Cys Lys Asp
                725                 730                 735
Cys Gly Lys Ala Phe Ser
            740

<210> SEQ ID NO 2
<211> LENGTH: 442
```

```
<212> TYPE: PRT
<213> ORGANISM: Homo sapiens
<300> PUBLICATION INFORMATION:
<308> DATABASE ACCESSION NUMBER: SWISS-PROT/Q9BY67
<309> DATABASE ENTRY DATE: 2007-06-26
<313> RELEVANT RESIDUES IN SEQ ID NO: (1)..(442)

<400> SEQUENCE: 2

Met Ala Ser Val Val Leu Pro Ser Gly Ser Gln Cys Ala Ala Ala
1               5                   10                  15

Ala Ala Ala Ala Pro Pro Gly Leu Arg Leu Arg Leu Leu Leu Leu
                20                  25                  30

Phe Ser Ala Ala Ala Leu Ile Pro Thr Gly Asp Gly Gln Asn Leu Phe
                35                  40                  45

Thr Lys Asp Val Thr Val Ile Glu Gly Glu Val Ala Thr Ile Ser Cys
50                      55                  60

Gln Val Asn Lys Ser Asp Asp Ser Val Ile Gln Leu Leu Asn Pro Asn
65                  70                  75                  80

Arg Gln Thr Ile Tyr Phe Arg Asp Phe Arg Pro Leu Lys Asp Ser Arg
                85                  90                  95

Phe Gln Leu Leu Asn Phe Ser Ser Glu Leu Lys Val Ser Leu Thr
                100                 105                 110

Asn Val Ser Ile Ser Asp Glu Gly Arg Tyr Phe Cys Gln Leu Tyr Thr
                115                 120                 125

Asp Pro Pro Gln Glu Ser Tyr Thr Thr Ile Thr Val Leu Val Pro Pro
130                 135                 140

Arg Asn Leu Met Ile Asp Ile Gln Lys Asp Thr Ala Val Glu Gly Glu
145                 150                 155                 160

Glu Ile Glu Val Asn Cys Thr Ala Met Ala Ser Lys Pro Ala Thr Thr
                165                 170                 175

Ile Arg Trp Phe Lys Gly Asn Thr Glu Leu Lys Gly Lys Ser Glu Val
                180                 185                 190

Glu Glu Trp Ser Asp Met Tyr Thr Val Thr Ser Gln Leu Met Leu Lys
                195                 200                 205

Val His Lys Glu Asp Asp Gly Val Pro Val Ile Cys Gln Val Glu His
    210                 215                 220

Pro Ala Val Thr Gly Asn Leu Gln Thr Gln Arg Tyr Leu Glu Val Gln
225                 230                 235                 240

Tyr Lys Pro Gln Val His Ile Gln Met Thr Tyr Pro Leu Gln Gly Leu
                245                 250                 255

Thr Arg Glu Gly Asp Ala Leu Glu Leu Thr Cys Glu Ala Ile Gly Lys
                260                 265                 270

Pro Gln Pro Val Met Val Thr Trp Val Arg Val Asp Asp Glu Met Pro
                275                 280                 285

Gln His Ala Val Leu Ser Gly Pro Asn Leu Phe Ile Asn Asn Leu Asn
    290                 295                 300

Lys Thr Asp Asn Gly Thr Tyr Arg Cys Glu Ala Ser Asn Ile Val Gly
305                 310                 315                 320

Lys Ala His Ser Asp Tyr Met Leu Tyr Val Tyr Asp Pro Pro Thr Thr
                325                 330                 335

Ile Pro Pro Pro Thr Thr Thr Thr Thr Thr Thr Thr Thr Thr Thr Thr
                340                 345                 350

Thr Ile Leu Thr Ile Ile Thr Asp Ser Arg Ala Gly Glu Glu Gly Ser
                355                 360                 365

Ile Arg Ala Val Asp His Ala Val Ile Gly Gly Val Val Ala Val Val
370                 375                 380
```

Val Phe Ala Met Leu Cys Leu Leu Ile Ile Leu Gly Arg Tyr Phe Ala
385                 390                 395                 400

Arg His Lys Gly Thr Tyr Phe Thr His Glu Ala Lys Gly Ala Asp Asp
                405                 410                 415

Ala Ala Asp Ala Asp Thr Ala Ile Ile Asn Ala Glu Gly Gln Asn
            420                 425                 430

Asn Ser Glu Glu Lys Lys Glu Tyr Phe Ile
        435                 440

<210> SEQ ID NO 3
<211> LENGTH: 392
<212> TYPE: PRT
<213> ORGANISM: Homo sapiens
<300> PUBLICATION INFORMATION:
<308> DATABASE ACCESSION NUMBER: SWISS-PROT/Q8NB57
<309> DATABASE ENTRY DATE: 2004-08-16
<313> RELEVANT RESIDUES IN SEQ ID NO: (1)..(392)

<400> SEQUENCE: 3

Met Ala Thr Ala Ala Gln Gly Pro Leu Ser Leu Leu Trp Gly Trp Leu
1               5                   10                  15

Trp Ser Glu Arg Phe Trp Leu Pro Glu Asn Val Ser Trp Ala Asp Leu
            20                  25                  30

Glu Gly Pro Ala Asp Gly Tyr Gly Tyr Pro Arg Gly Arg His Ile Leu
        35                  40                  45

Ser Val Phe Pro Leu Ala Ala Gly Ile Phe Phe Val Arg Leu Leu Phe
    50                  55                  60

Glu Arg Phe Ile Ala Lys Pro Cys Ala Leu Cys Ile Gly Ile Glu Asp
65                  70                  75                  80

Ser Gly Pro Tyr Gln Ala Gln Pro Asn Ala Ile Leu Glu Lys Val Phe
                85                  90                  95

Ile Ser Ile Thr Lys Tyr Pro Asp Lys Lys Arg Leu Glu Gly Leu Ser
            100                 105                 110

Lys Gln Leu Asp Trp Asn Val Arg Lys Ile Gln Cys Trp Phe Arg His
        115                 120                 125

Arg Arg Asn Gln Asp Lys Pro Pro Thr Leu Thr Lys Phe Cys Glu Ser
130                 135                 140

Met Trp Arg Phe Thr Phe Tyr Leu Cys Ile Phe Cys Tyr Gly Ile Arg
145                 150                 155                 160

Phe Leu Trp Ser Ser Pro Trp Phe Trp Asp Ile Arg Gln Cys Trp His
                165                 170                 175

Asn Tyr Pro Phe Gln Pro Leu Ser Ser Gly Leu Tyr His Tyr Tyr Ile
            180                 185                 190

Met Glu Leu Ala Phe Tyr Trp Ser Leu Met Phe Ser Gln Phe Thr Asp
        195                 200                 205

Ile Lys Arg Lys Asp Phe Leu Ile Met Phe Val His His Leu Val Thr
    210                 215                 220

Ile Gly Leu Ile Ser Phe Ser Tyr Ile Asn Asn Met Val Arg Val Gly
225                 230                 235                 240

Thr Leu Ile Met Cys Leu His Asp Val Ser Asp Phe Leu Leu Glu Ala
                245                 250                 255

Ala Lys Leu Ala Asn Tyr Ala Lys Tyr Gln Arg Leu Cys Asp Thr Leu
            260                 265                 270

Phe Val Ile Phe Ser Ala Val Phe Met Val Thr Arg Leu Gly Ile Tyr
        275                 280                 285

Pro Phe Trp Ile Leu Asn Thr Thr Leu Phe Glu Ser Trp Glu Ile Ile

-continued

```
            290                 295                 300
Gly Pro Tyr Ala Ser Trp Trp Leu Leu Asn Gly Leu Leu Thr Leu
305                 310                 315                 320

Gln Leu Leu His Val Ile Trp Ser Tyr Leu Ile Ala Arg Ile Ala Leu
                325                 330                 335

Lys Ala Leu Ile Arg Gly Lys Val Ser Lys Asp Asp Arg Ser Asp Val
                340                 345                 350

Glu Ser Ser Ser Glu Glu Glu Asp Val Thr Thr Cys Thr Lys Ser Pro
                355                 360                 365

Cys Asp Ser Ser Ser Asn Gly Ala Asn Arg Val Asn Gly His Met
                370                 375                 380

Gly Gly Ser Tyr Trp Ala Glu Glu
385                 390
```

<210> SEQ ID NO 4
<211> LENGTH: 393
<212> TYPE: PRT
<213> ORGANISM: Homo sapiens
<300> PUBLICATION INFORMATION:
<308> DATABASE ACCESSION NUMBER: SWISS-PROT/Q2XN98
<309> DATABASE ENTRY DATE: 2005-12-20
<313> RELEVANT RESIDUES IN SEQ ID NO: (1)..(393)

<400> SEQUENCE: 4

```
Met Glu Glu Pro Gln Ser Asp Pro Ser Val Glu Pro Pro Leu Ser Gln
1               5                   10                  15

Glu Thr Phe Ser Asp Leu Trp Lys Leu Leu Pro Glu Asn Asn Val Leu
                20                  25                  30

Ser Pro Leu Pro Ser Gln Ala Met Asp Asp Leu Met Leu Ser Pro Asp
                35                  40                  45

Asp Ile Glu Gln Trp Phe Thr Glu Asp Pro Gly Pro Asp Glu Ala Pro
            50                  55                  60

Arg Met Pro Glu Ala Ala Pro Pro Val Ala Pro Ala Pro Ala Ala Pro
65                  70                  75                  80

Thr Pro Ala Ala Pro Ala Pro Ala Pro Ser Trp Pro Leu Ser Ser Ser
                85                  90                  95

Val Pro Ser Gln Lys Thr Tyr Gln Gly Ser Tyr Gly Phe Arg Leu Gly
                100                 105                 110

Phe Leu His Ser Gly Thr Ala Lys Ser Val Thr Cys Thr Tyr Ser Pro
                115                 120                 125

Ala Leu Asn Lys Met Phe Cys Gln Leu Ala Lys Thr Cys Pro Val Gln
            130                 135                 140

Leu Trp Val Asp Ser Thr Pro Pro Pro Gly Thr Arg Val Arg Ala Met
145                 150                 155                 160

Ala Ile Tyr Lys Gln Ser Gln His Met Thr Glu Val Val Arg Arg Cys
                165                 170                 175

Pro His His Glu Arg Cys Ser Asp Ser Asp Gly Leu Ala Pro Pro Gln
                180                 185                 190

His Leu Ile Arg Val Glu Gly Asn Leu Arg Val Glu Tyr Leu Asp Asp
            195                 200                 205

Arg Asn Thr Phe Arg His Ser Val Val Val Pro Tyr Glu Pro Pro Glu
            210                 215                 220

Val Gly Ser Asp Cys Thr Thr Ile His Tyr Asn Tyr Met Cys Asn Ser
225                 230                 235                 240

Ser Cys Met Gly Gly Met Asn Arg Arg Pro Ile Leu Thr Ile Ile Thr
                245                 250                 255
```

-continued

```
Leu Glu Asp Ser Ser Gly Asn Leu Leu Gly Arg Asn Ser Phe Glu Val
                260                 265                 270

Arg Val Cys Ala Cys Pro Gly Arg Asp Arg Arg Thr Glu Glu Glu Asn
                275                 280                 285

Leu Arg Lys Lys Gly Glu Pro His His Glu Leu Pro Pro Gly Ser Thr
            290                 295                 300

Lys Arg Ala Leu Pro Asn Asn Thr Ser Ser Pro Gln Pro Lys Lys
305                 310                 315                 320

Lys Pro Leu Asp Gly Glu Tyr Phe Thr Leu Gln Ile Arg Gly Arg Glu
                325                 330                 335

Arg Phe Glu Met Phe Arg Glu Leu Asn Glu Ala Leu Glu Leu Lys Asp
                340                 345                 350

Ala Gln Ala Gly Lys Glu Pro Gly Gly Ser Arg Ala His Ser Ser His
            355                 360                 365

Leu Lys Ser Lys Lys Gly Gln Ser Thr Ser Arg His Lys Lys Leu Met
    370                 375                 380

Phe Lys Thr Glu Gly Pro Asp Ser Asp
385                 390

<210> SEQ ID NO 5
<211> LENGTH: 540
<212> TYPE: PRT
<213> ORGANISM: Homo sapiens
<300> PUBLICATION INFORMATION:
<308> DATABASE ACCESSION NUMBER: SWISS-PROT/Q96CX4
<309> DATABASE ENTRY DATE: 2007-09-11
<313> RELEVANT RESIDUES IN SEQ ID NO: (1)..(540)

<400> SEQUENCE: 5

Met Glu Arg Glu Ala Leu Pro Trp Gly Leu Glu Pro Gln Asp Val Gln
1               5                   10                  15

Ser Ser Asp Glu Met Arg Ser Pro Glu Gly Tyr Leu Arg Gly Asn Met
                20                  25                  30

Ser Glu Asn Glu Glu Glu Glu Ile Ser Gln Gln Glu Gly Ser Gly Asp
            35                  40                  45

Tyr Glu Val Glu Glu Ile Pro Phe Gly Leu Glu Pro Gln Ser Pro Gly
    50                  55                  60

Phe Glu Pro Gln Ser Pro Glu Phe Glu Pro Gln Ser Pro Arg Phe Glu
65                  70                  75                  80

Pro Glu Ser Pro Gly Phe Glu Ser Arg Ser Pro Gly Leu Val Pro Pro
                85                  90                  95

Ser Pro Glu Phe Ala Pro Arg Ser Pro Glu Ser Asp Ser Gln Ser Pro
            100                 105                 110

Glu Phe Glu Ser Gln Ser Pro Arg Tyr Glu Pro Gln Ser Pro Gly Tyr
        115                 120                 125

Glu Pro Arg Ser Pro Gly Tyr Glu Pro Arg Ser Pro Gly Tyr Glu Ser
    130                 135                 140

Glu Ser Ser Arg Tyr Glu Ser Gln Asn Thr Glu Leu Lys Thr Gln Ser
145                 150                 155                 160

Pro Glu Phe Glu Ala Gln Ser Ser Lys Phe Glu Gly Ala Glu Met
                165                 170                 175

Leu Leu Asn Pro Glu Glu Lys Ser Pro Leu Asn Ile Ser Val Gly Val
            180                 185                 190

His Pro Leu Asp Ser Phe Thr Gln Gly Phe Gly Glu Gln Pro Thr Gly
        195                 200                 205

Asp Leu Pro Ile Gly Pro Pro Phe Glu Met Pro Thr Gly Ala Leu Leu
    210                 215                 220
```

```
Ser Thr Pro Gln Phe Glu Met Leu Gln Asn Pro Leu Gly Leu Thr Gly
225                 230                 235                 240

Ala Leu Arg Gly Pro Gly Arg Gly Gly Arg Ala Arg Gly Gly Gln
            245                 250                 255

Gly Pro Arg Pro Asn Ile Cys Gly Ile Cys Gly Lys Ser Phe Gly Arg
            260                 265                 270

Gly Ser Thr Leu Ile Gln His Gln Arg Ile His Thr Gly Glu Lys Pro
        275                 280                 285

Tyr Lys Cys Glu Val Cys Ser Lys Ala Phe Ser Gln Ser Ser Asp Leu
    290                 295                 300

Ile Lys His Gln Arg Thr His Thr Gly Glu Arg Pro Tyr Lys Cys Pro
305                 310                 315                 320

Arg Cys Gly Lys Ala Phe Ala Asp Ser Ser Tyr Leu Leu Arg His Gln
                325                 330                 335

Arg Thr His Ser Gly Gln Lys Pro Tyr Lys Cys Pro His Cys Gly Lys
            340                 345                 350

Ala Phe Gly Asp Ser Ser Tyr Leu Leu Arg His Gln Arg Thr His Ser
        355                 360                 365

His Glu Arg Pro Tyr Ser Cys Thr Glu Cys Gly Lys Cys Tyr Ser Gln
    370                 375                 380

Asn Ser Ser Leu Arg Ser His Gln Arg Val His Thr Gly Gln Arg Pro
385                 390                 395                 400

Phe Ser Cys Gly Ile Cys Gly Lys Ser Phe Ser Gln Arg Ser Ala Leu
                405                 410                 415

Ile Pro His Ala Arg Ser His Ala Arg Glu Lys Pro Phe Lys Cys Pro
            420                 425                 430

Glu Cys Gly Lys Arg Phe Gly Gln Ser Ser Val Leu Ala Ile His Ala
        435                 440                 445

Arg Thr His Leu Pro Gly Arg Thr Tyr Ser Cys Pro Asp Cys Gly Lys
    450                 455                 460

Thr Phe Asn Arg Ser Ser Thr Leu Ile Gln His Gln Arg Ser His Thr
465                 470                 475                 480

Gly Glu Arg Pro Tyr Arg Cys Ala Val Cys Gly Lys Gly Phe Cys Arg
                485                 490                 495

Ser Ser Thr Leu Leu Gln His Arg Val His Ser Gly Glu Arg Pro
            500                 505                 510

Tyr Lys Cys Asp Asp Cys Gly Lys Ala Phe Ser Gln Ser Ser Asp Leu
    515                 520                 525

Ile Arg His Gln Arg Thr His Ala Ala Gly Arg Arg
530                 535                 540

<210> SEQ ID NO 6
<211> LENGTH: 1978
<212> TYPE: PRT
<213> ORGANISM: Homo sapiens
<300> PUBLICATION INFORMATION:
<308> DATABASE ACCESSION NUMBER: SWISS-PROT/Q14966
<309> DATABASE ENTRY DATE: 2005-07-19
<313> RELEVANT RESIDUES IN SEQ ID NO: (1)..(1978)

<400> SEQUENCE: 6

Met Ser Arg Pro Arg Phe Asn Pro Arg Gly Asp Phe Pro Leu Gln Arg
1               5                   10                  15

Pro Arg Ala Pro Asn Pro Ser Gly Met Arg Pro Pro Gly Pro Phe Met
            20                  25                  30

Arg Pro Gly Ser Met Gly Leu Pro Arg Phe Tyr Pro Ala Gly Arg Ala
```

```
            35                  40                  45
Arg Gly Ile Pro His Arg Phe Ala Gly His Glu Ser Tyr Gln Asn Met
 50                  55                  60

Gly Pro Gln Arg Met Asn Val Gln Val Thr Gln His Arg Thr Asp Pro
 65                  70                  75                  80

Arg Leu Thr Lys Glu Lys Leu Asp Phe His Glu Ala Gln Gln Lys Lys
                     85                  90                  95

Gly Lys Pro His Gly Ser Arg Trp Asp Glu Pro His Ile Ser Ala
                100                 105                 110

Ser Val Ala Val Lys Gln Ser Ser Val Thr Gln Val Thr Glu Gln Ser
                115                 120                 125

Pro Lys Val Gln Ser Arg Tyr Thr Lys Glu Ser Ala Ser Ser Ile Leu
                130                 135                 140

Ala Ser Phe Gly Leu Ser Asn Glu Asp Leu Glu Glu Leu Ser Arg Tyr
145                 150                 155                 160

Pro Asp Glu Gln Leu Thr Pro Glu Asn Met Pro Leu Ile Leu Arg Asp
                165                 170                 175

Ile Arg Met Arg Lys Met Gly Arg Arg Leu Pro Asn Leu Pro Ser Gln
                180                 185                 190

Ser Arg Asn Lys Glu Thr Leu Gly Ser Glu Ala Val Ser Ser Asn Val
                195                 200                 205

Ile Asp Tyr Gly His Ala Ser Lys Tyr Gly Tyr Thr Glu Asp Pro Leu
                210                 215                 220

Glu Val Arg Ile Tyr Asp Pro Glu Ile Pro Thr Asp Glu Val Glu Asn
225                 230                 235                 240

Glu Phe Gln Ser Gln Gln Asn Ile Ser Ala Ser Val Pro Asn Pro Asn
                245                 250                 255

Val Ile Cys Asn Ser Met Phe Pro Val Glu Asp Val Phe Arg Gln Met
                260                 265                 270

Asp Phe Pro Gly Glu Ser Ser Asn Asn Arg Ser Phe Phe Ser Val Glu
                275                 280                 285

Ser Gly Thr Lys Met Ser Gly Leu His Ile Ser Gly Gly Gln Ser Val
                290                 295                 300

Leu Glu Pro Ile Lys Ser Val Asn Gln Ser Ile Asn Gln Thr Val Ser
305                 310                 315                 320

Gln Thr Met Ser Gln Ser Leu Ile Pro Pro Ser Met Asn Gln Gln Pro
                325                 330                 335

Phe Ser Ser Glu Leu Ile Ser Ser Val Ser Gln Gln Glu Arg Ile Pro
                340                 345                 350

His Glu Pro Val Ile Asn Ser Ser Asn Val His Val Gly Ser Arg Gly
                355                 360                 365

Ser Lys Lys Asn Tyr Gln Ser Gln Ala Asp Ile Pro Ile Arg Ser Pro
                370                 375                 380

Phe Gly Ile Val Lys Ala Ser Trp Leu Pro Lys Phe Ser His Ala Asp
385                 390                 395                 400

Ala Gln Lys Met Lys Arg Leu Pro Thr Pro Ser Met Met Asn Asp Tyr
                405                 410                 415

Tyr Ala Ala Ser Pro Arg Ile Phe Pro His Leu Cys Ser Leu Cys Asn
                420                 425                 430

Val Glu Cys Ser His Leu Lys Asp Trp Ile Gln His Gln Asn Thr Ser
                435                 440                 445

Thr His Ile Glu Ser Cys Arg Gln Leu Arg Gln Gln Tyr Pro Asp Trp
                450                 455                 460
```

-continued

```
Asn Pro Glu Ile Leu Pro Ser Arg Arg Asn Glu Gly Asn Arg Lys Glu
465                 470                 475                 480

Asn Glu Thr Pro Arg Arg Ser His Ser Pro Ser Pro Arg Ser
                485                 490                 495

Arg Arg Ser Ser Ser Ser His Arg Phe Arg Arg Ser Arg Ser Pro Met
            500                 505                 510

His Tyr Met Tyr Arg Pro Arg Ser Arg Ser Pro Arg Ile Cys His Arg
            515                 520                 525

Phe Ile Ser Arg Tyr Arg Ser Arg Ser Arg Ser Pro Tyr Arg
        530                 535                 540

Ile Arg Asn Pro Phe Arg Gly Ser Pro Lys Cys Phe Arg Ser Val Ser
545                 550                 555                 560

Pro Glu Arg Met Ser Arg Arg Ser Val Arg Ser Ser Asp Arg Lys Lys
                565                 570                 575

Ala Leu Glu Asp Val Val Gln Arg Ser Gly His Gly Thr Glu Phe Asn
            580                 585                 590

Lys Gln Lys His Leu Glu Ala Ala Asp Lys Gly His Ser Pro Ala Gln
            595                 600                 605

Lys Pro Lys Thr Ser Ser Gly Thr Lys Pro Ser Val Lys Pro Thr Ser
        610                 615                 620

Ala Thr Lys Ser Asp Ser Asn Leu Gly Gly His Ser Ile Arg Cys Lys
625                 630                 635                 640

Ser Lys Asn Leu Glu Asp Asp Thr Leu Ser Glu Cys Lys Gln Val Ser
                645                 650                 655

Asp Lys Ala Val Ser Leu Gln Arg Lys Leu Arg Lys Glu Gln Ser Leu
            660                 665                 670

His Tyr Gly Ser Val Leu Leu Ile Thr Glu Leu Pro Glu Asp Gly Cys
        675                 680                 685

Thr Glu Glu Asp Val Arg Lys Leu Phe Gln Pro Phe Gly Lys Val Asn
            690                 695                 700

Asp Val Leu Ile Val Pro Tyr Arg Lys Glu Ala Tyr Leu Glu Met Glu
705                 710                 715                 720

Phe Lys Glu Ala Ile Thr Ala Ile Met Lys Tyr Ile Glu Thr Thr Pro
                725                 730                 735

Leu Thr Ile Lys Gly Lys Ser Val Lys Ile Cys Val Pro Gly Lys Lys
            740                 745                 750

Lys Ala Gln Asn Lys Glu Val Lys Lys Thr Leu Glu Ser Lys Lys
        755                 760                 765

Val Ser Ala Ser Thr Leu Lys Arg Asp Ala Asp Ala Ser Lys Ala Val
770                 775                 780

Glu Ile Val Thr Ser Thr Ser Ala Ala Lys Thr Gly Gln Ala Lys Ala
785                 790                 795                 800

Ser Val Ala Lys Val Asn Lys Ser Thr Gly Lys Ser Ala Ser Ser Val
                805                 810                 815

Lys Ser Val Val Thr Val Ala Val Lys Gly Asn Lys Ala Ser Ile Lys
            820                 825                 830

Thr Ala Lys Ser Gly Gly Lys Lys Ser Leu Glu Ala Lys Lys Thr Gly
        835                 840                 845

Asn Val Lys Asn Lys Asp Ser Asn Lys Pro Val Thr Ile Pro Glu Asn
850                 855                 860

Ser Glu Ile Lys Thr Ser Ile Glu Val Lys Ala Thr Glu Asn Cys Ala
865                 870                 875                 880

Lys Glu Ala Ile Ser Asp Ala Ala Leu Glu Ala Thr Glu Asn Glu Pro
                885                 890                 895
```

```
Leu Asn Lys Glu Thr Glu Glu Met Cys Val Met Leu Val Ser Asn Leu
        900                 905                 910

Pro Asn Lys Gly Tyr Ser Val Glu Glu Val Tyr Asp Leu Ala Lys Pro
        915                 920                 925

Phe Gly Gly Leu Lys Asp Ile Leu Ile Leu Ser Ser His Lys Lys Ala
        930                 935                 940

Tyr Ile Glu Ile Asn Arg Lys Ala Ala Glu Ser Met Val Lys Phe Tyr
945                 950                 955                 960

Thr Cys Phe Pro Val Leu Met Asp Gly Asn Gln Leu Ser Ile Ser Met
                965                 970                 975

Ala Pro Glu Asn Met Asn Ile Lys Asp Glu Glu Ala Ile Phe Ile Thr
        980                 985                 990

Leu Val Lys Glu Asn Asp Pro Glu Ala Asn Ile Asp Thr Ile Tyr Asp
        995                 1000                1005

Arg Phe Val His Leu Asp Asn Leu Pro Glu Asp Gly Leu Gln Cys
        1010                1015                1020

Val Leu Cys Val Gly Leu Gln Phe Gly Lys Val Asp His His Val
        1025                1030                1035

Phe Ile Ser Asn Arg Asn Lys Ala Ile Leu Gln Leu Asp Ser Pro
        1040                1045                1050

Glu Ser Ala Gln Ser Met Tyr Ser Phe Leu Lys Gln Asn Pro Gln
        1055                1060                1065

Asn Ile Gly Asp His Met Leu Thr Cys Ser Leu Ser Pro Lys Ile
        1070                1075                1080

Asp Leu Pro Glu Val Gln Ile Glu His Asp Pro Glu Leu Glu Lys
        1085                1090                1095

Glu Ser Pro Gly Leu Lys Asn Ser Pro Ile Asp Glu Ser Glu Val
        1100                1105                1110

Gln Thr Ala Thr Asp Ser Pro Ser Val Lys Pro Asn Glu Leu Glu
        1115                1120                1125

Glu Glu Ser Thr Pro Ser Ile Gln Thr Glu Thr Leu Val Gln Gln
        1130                1135                1140

Glu Glu Pro Cys Glu Glu Glu Ala Glu Lys Ala Thr Cys Asp Ser
        1145                1150                1155

Asp Phe Ala Val Glu Thr Leu Glu Leu Glu Thr Gln Gly Glu Glu
        1160                1165                1170

Val Lys Glu Glu Ile Pro Leu Val Ala Ser Ala Ser Val Ser Ile
        1175                1180                1185

Glu Gln Phe Thr Glu Asn Ala Glu Glu Cys Ala Leu Asn Gln Gln
        1190                1195                1200

Met Phe Asn Ser Asp Leu Glu Lys Lys Gly Ala Glu Ile Ile Asn
        1205                1210                1215

Pro Lys Thr Ala Leu Leu Pro Ser Asp Ser Val Phe Ala Glu Glu
        1220                1225                1230

Arg Asn Leu Lys Gly Ile Leu Glu Glu Ser Pro Ser Glu Ala Glu
        1235                1240                1245

Asp Phe Ile Ser Gly Ile Thr Gln Thr Met Val Glu Ala Val Ala
        1250                1255                1260

Glu Val Glu Lys Asn Glu Thr Val Ser Glu Ile Leu Pro Ser Thr
        1265                1270                1275

Cys Ile Val Thr Leu Val Pro Gly Ile Pro Thr Gly Asp Glu Lys
        1280                1285                1290

Thr Val Asp Lys Lys Asn Ile Ser Glu Lys Lys Gly Asn Met Asp
```

-continued

```
        1295                1300                1305

Glu Lys Glu Glu Lys Glu Phe Asn Thr Lys Glu Thr Arg Met Asp
    1310                1315                1320

Leu Gln Ile Gly Thr Glu Lys Ala Glu Lys Asn Glu Gly Arg Met
    1325                1330                1335

Asp Ala Glu Lys Val Glu Lys Met Ala Ala Met Lys Glu Lys Pro
    1340                1345                1350

Ala Glu Asn Thr Leu Phe Lys Ala Tyr Pro Asn Lys Gly Val Gly
    1355                1360                1365

Gln Ala Asn Lys Pro Asp Glu Thr Ser Lys Thr Ser Ile Leu Ala
    1370                1375                1380

Val Ser Asp Val Ser Ser Lys Pro Ser Ile Lys Ala Val Ile
    1385                1390                1395

Val Ser Ser Pro Lys Ala Lys Ala Thr Val Ser Lys Thr Glu Asn
    1400                1405                1410

Gln Lys Ser Phe Pro Lys Ser Val Pro Arg Asp Gln Ile Asn Ala
    1415                1420                1425

Glu Lys Lys Leu Ser Ala Lys Glu Phe Gly Leu Lys Pro Thr
    1430                1435                1440

Ser Ala Arg Ser Gly Leu Ala Glu Ser Ser Lys Phe Lys Pro
    1445                1450                1455

Thr Gln Ser Ser Leu Thr Arg Gly Gly Ser Gly Arg Ile Ser Ala
    1460                1465                1470

Leu Gln Gly Lys Leu Ser Lys Leu Asp Tyr Arg Asp Ile Thr Lys
    1475                1480                1485

Gln Ser Gln Glu Thr Glu Ala Arg Pro Ser Ile Met Lys Arg Asp
    1490                1495                1500

Asp Ser Asn Asn Lys Thr Leu Ala Glu Gln Asn Thr Lys Asn Pro
    1505                1510                1515

Lys Ser Thr Thr Gly Arg Ser Ser Lys Ser Lys Glu Glu Pro Leu
    1520                1525                1530

Phe Pro Phe Asn Leu Asp Glu Phe Val Thr Val Asp Glu Val Ile
    1535                1540                1545

Glu Glu Val Asn Pro Ser Gln Ala Lys Gln Asn Pro Leu Lys Gly
    1550                1555                1560

Lys Arg Lys Glu Thr Leu Lys Asn Val Pro Phe Ser Glu Leu Asn
    1565                1570                1575

Leu Lys Lys Lys Gly Lys Thr Ser Thr Pro Arg Gly Val Glu
    1580                1585                1590

Gly Glu Leu Ser Phe Val Thr Leu Asp Glu Ile Gly Glu Glu Glu
    1595                1600                1605

Asp Ala Ala Ala His Leu Ala Gln Ala Leu Val Thr Val Asp Glu
    1610                1615                1620

Val Ile Asp Glu Glu Glu Leu Asn Met Glu Glu Met Val Lys Asn
    1625                1630                1635

Ser Asn Ser Leu Phe Thr Leu Asp Glu Leu Ile Asp Gln Asp Asp
    1640                1645                1650

Cys Ile Ser His Ser Glu Pro Lys Asp Val Thr Val Leu Ser Val
    1655                1660                1665

Ala Glu Glu Gln Asp Leu Leu Lys Gln Glu Arg Leu Val Thr Val
    1670                1675                1680

Asp Glu Ile Gly Glu Val Glu Glu Leu Pro Leu Asn Glu Ser Ala
    1685                1690                1695
```

Asp Ile Thr Phe Ala Thr Leu Asn Thr Lys Gly Asn Glu Gly Asp
1700            1705                1710

Thr Val Arg Asp Ser Ile Gly Phe Ile Ser Ser Gln Val Pro Glu
1715            1720                1725

Asp Pro Ser Thr Leu Val Val Asp Glu Ile Gln Asp Asp Ser
1730            1735                1740

Ser Asp Leu His Leu Val Thr Leu Asp Glu Val Thr Glu Glu Asp
1745            1750                1755

Glu Asp Ser Leu Ala Asp Phe Asn Asn Leu Lys Glu Glu Leu Asn
1760            1765                1770

Phe Val Thr Val Asp Glu Val Gly Glu Glu Glu Asp Gly Asp Asn
1775            1780                1785

Asp Leu Lys Val Glu Leu Ala Gln Ser Lys Asn Asp His Pro Thr
1790            1795                1800

Asp Lys Lys Gly Asn Arg Lys Lys Arg Ala Val Asp Thr Lys Lys
1805            1810                1815

Thr Lys Leu Glu Ser Leu Ser Gln Val Gly Pro Val Asn Glu Asn
1820            1825                1830

Val Met Glu Glu Asp Leu Lys Thr Met Ile Glu Arg His Leu Thr
1835            1840                1845

Ala Lys Thr Pro Thr Lys Arg Val Arg Ile Gly Lys Thr Leu Pro
1850            1855                1860

Ser Glu Lys Ala Val Val Thr Glu Pro Ala Lys Gly Glu Glu Ala
1865            1870                1875

Phe Gln Met Ser Glu Val Asp Glu Glu Ser Gly Leu Lys Asp Ser
1880            1885                1890

Glu Pro Glu Arg Lys Arg Lys Lys Thr Glu Asp Ser Ser Ser Gly
1895            1900                1905

Lys Ser Val Ala Ser Asp Val Pro Glu Glu Leu Asp Phe Leu Val
1910            1915                1920

Pro Lys Ala Gly Phe Phe Cys Pro Ile Cys Ser Leu Phe Tyr Ser
1925            1930                1935

Gly Glu Lys Ala Met Thr Asn His Cys Lys Ser Thr Arg His Lys
1940            1945                1950

Gln Asn Thr Glu Lys Phe Met Ala Lys Gln Arg Lys Glu Lys Glu
1955            1960                1965

Gln Asn Glu Ala Glu Glu Arg Ser Ser Arg
1970            1975

<210> SEQ ID NO 7
<211> LENGTH: 237
<212> TYPE: PRT
<213> ORGANISM: Homo sapiens
<300> PUBLICATION INFORMATION:
<308> DATABASE ACCESSION NUMBER: SWISS-PROT/P54105
<309> DATABASE ENTRY DATE: 1996-10-01
<313> RELEVANT RESIDUES IN SEQ ID NO: (1)..(237)

<400> SEQUENCE: 7

Met Ser Phe Leu Lys Ser Phe Pro Pro Gly Pro Ala Glu Gly Leu
1               5                   10                  15

Leu Arg Gln Gln Pro Asp Thr Glu Ala Val Leu Asn Gly Lys Gly Leu
        20                  25                  30

Gly Thr Gly Thr Leu Tyr Ile Ala Glu Ser Arg Leu Ser Trp Leu Asp
            35                  40                  45

Gly Ser Gly Leu Gly Phe Ser Leu Glu Tyr Pro Thr Ile Ser Leu His
        50                  55                  60

```
Ala Leu Ser Arg Asp Arg Ser Asp Cys Leu Gly Glu His Leu Tyr Val
 65                  70                  75                  80

Met Val Asn Ala Lys Phe Glu Glu Ser Lys Glu Pro Val Ala Asp
                 85                  90                  95

Glu Glu Glu Glu Asp Ser Asp Asp Val Glu Pro Ile Thr Glu Phe
            100                 105                 110

Arg Phe Val Pro Ser Asp Lys Ser Ala Leu Glu Ala Met Phe Thr Ala
            115                 120                 125

Met Cys Glu Cys Gln Ala Leu His Pro Asp Pro Glu Asp Glu Asp Ser
130                 135                 140

Asp Asp Tyr Asp Gly Glu Glu Tyr Asp Val Glu Ala His Glu Gln Gly
145                 150                 155                 160

Gln Gly Asp Ile Pro Thr Phe Tyr Thr Tyr Glu Glu Gly Leu Ser His
                165                 170                 175

Leu Thr Ala Glu Gly Gln Ala Thr Leu Glu Arg Leu Glu Gly Met Leu
            180                 185                 190

Ser Gln Ser Val Ser Ser Gln Tyr Asn Met Ala Gly Val Arg Thr Glu
            195                 200                 205

Asp Ser Ile Arg Asp Tyr Glu Asp Gly Met Glu Val Asp Thr Thr Pro
210                 215                 220

Thr Val Ala Gly Gln Phe Glu Asp Ala Asp Val Asp His
225                 230                 235

<210> SEQ ID NO 8
<211> LENGTH: 294
<212> TYPE: PRT
<213> ORGANISM: Homo sapiens
<300> PUBLICATION INFORMATION:
<308> DATABASE ACCESSION NUMBER: SWISS-PROT/Q9UL40
<309> DATABASE ENTRY DATE: 2005-10-25
<313> RELEVANT RESIDUES IN SEQ ID NO: (1)..(294)

<400> SEQUENCE: 8

Met Glu Tyr Pro Ala Pro Ala Thr Val Gln Ala Ala Asp Gly Gly Ala
  1               5                  10                  15

Ala Gly Pro Tyr Ser Ser Glu Leu Leu Glu Gly Gln Glu Pro Asp
             20                  25                  30

Gly Val Arg Phe Asp Arg Glu Arg Ala Arg Leu Trp Glu Ala Val
         35                  40                  45

Ser Gly Ala Gln Pro Val Gly Arg Glu Glu Val Glu His Met Ile Gln
 50                  55                  60

Lys Asn Gln Cys Leu Phe Thr Asn Thr Gln Cys Lys Val Cys Cys Ala
 65                  70                  75                  80

Leu Leu Ile Ser Glu Ser Gln Lys Leu Ala His Tyr Gln Ser Lys Lys
                 85                  90                  95

His Ala Asn Lys Val Lys Arg Tyr Leu Ala Ile His Gly Met Glu Thr
            100                 105                 110

Leu Lys Gly Glu Thr Lys Lys Leu Asp Ser Asp Gln Lys Ser Ser Arg
            115                 120                 125

Ser Lys Asp Lys Asn Gln Cys Cys Pro Ile Cys Asn Met Thr Phe Ser
130                 135                 140

Ser Pro Val Val Ala Gln Ser His Tyr Leu Gly Lys Thr His Ala Lys
145                 150                 155                 160

Asn Leu Lys Leu Lys Gln Gln Ser Thr Lys Val Glu Ala Leu His Gln
                165                 170                 175

Asn Arg Glu Met Ile Asp Pro Asp Lys Phe Cys Ser Leu Cys His Ala
```

```
            180                 185                 190
Thr Phe Asn Asp Pro Val Met Ala Gln Gln His Tyr Val Gly Lys Lys
        195                 200                 205

His Arg Lys Gln Glu Thr Lys Leu Lys Leu Met Ala Arg Tyr Gly Arg
    210                 215                 220

Leu Ala Asp Pro Ala Val Thr Asp Phe Pro Ala Gly Lys Gly Tyr Pro
225                 230                 235                 240

Cys Lys Thr Cys Lys Ile Val Leu Asn Ser Ile Glu Gln Tyr Gln Ala
                245                 250                 255

His Val Ser Gly Phe Lys His Lys Asn Gln Ser Pro Lys Thr Val Ala
            260                 265                 270

Ser Ser Leu Gly Gln Ile Pro Met Gln Arg Gln Pro Ile Gln Lys Asp
        275                 280                 285

Ser Thr Thr Leu Glu Asp
    290

<210> SEQ ID NO 9
<211> LENGTH: 654
<212> TYPE: PRT
<213> ORGANISM: Homo sapiens
<300> PUBLICATION INFORMATION:
<308> DATABASE ACCESSION NUMBER: SWISS-PROT/P15923
<309> DATABASE ENTRY DATE: 1990-04-01
<313> RELEVANT RESIDUES IN SEQ ID NO: (1)..(654)

<400> SEQUENCE: 9

Met Asn Gln Pro Gln Arg Met Ala Pro Val Gly Thr Asp Lys Glu Leu
1               5                   10                  15

Ser Asp Leu Leu Asp Phe Ser Met Met Phe Pro Leu Pro Val Thr Asn
            20                  25                  30

Gly Lys Gly Arg Pro Ala Ser Leu Ala Gly Ala Gln Phe Gly Gly Ser
        35                  40                  45

Gly Leu Glu Asp Arg Pro Ser Gly Ser Trp Gly Ser Gly Asp Gln
    50                  55                  60

Ser Ser Ser Ser Phe Asp Pro Ser Arg Thr Phe Ser Glu Gly Thr His
65                  70                  75                  80

Phe Thr Glu Ser His Ser Ser Leu Ser Ser Thr Phe Leu Gly Pro
                85                  90                  95

Gly Leu Gly Gly Lys Ser Gly Glu Arg Gly Ala Tyr Ala Ser Phe Gly
            100                 105                 110

Arg Asp Ala Gly Val Gly Gly Leu Thr Gln Ala Gly Phe Leu Ser Gly
        115                 120                 125

Glu Leu Ala Leu Asn Ser Pro Gly Pro Leu Ser Pro Ser Gly Met Lys
    130                 135                 140

Gly Thr Ser Gln Tyr Tyr Pro Ser Tyr Ser Gly Ser Ser Arg Arg Arg
145                 150                 155                 160

Ala Ala Asp Gly Ser Leu Asp Thr Gln Pro Lys Lys Val Arg Lys Val
                165                 170                 175

Pro Pro Gly Leu Pro Ser Ser Val Tyr Pro Pro Ser Ser Gly Glu Asp
            180                 185                 190

Tyr Gly Arg Asp Ala Thr Ala Tyr Pro Ser Ala Lys Thr Pro Ser Ser
        195                 200                 205

Thr Tyr Pro Ala Pro Phe Tyr Val Ala Asp Gly Ser Leu His Pro Ser
    210                 215                 220

Ala Glu Leu Trp Ser Pro Pro Gly Gln Ala Gly Phe Gly Pro Met Leu
225                 230                 235                 240
```

```
Gly Gly Gly Ser Ser Pro Leu Pro Leu Pro Pro Gly Ser Gly Pro Val
                245                 250                 255
Gly Ser Ser Gly Ser Ser Ser Thr Phe Gly Gly Leu His Gln His Glu
            260                 265                 270
Arg Met Gly Tyr Gln Leu His Gly Ala Glu Val Asn Gly Gly Leu Pro
        275                 280                 285
Ser Ala Ser Ser Phe Ser Ser Ala Pro Gly Ala Thr Tyr Gly Gly Val
    290                 295                 300
Ser Ser His Thr Pro Pro Val Ser Gly Ala Asp Ser Leu Leu Gly Ser
305                 310                 315                 320
Arg Gly Thr Thr Ala Gly Ser Ser Gly Asp Ala Leu Gly Lys Ala Leu
                325                 330                 335
Ala Ser Ile Tyr Ser Pro Asp His Ser Ser Asn Asn Phe Ser Ser Ser
            340                 345                 350
Pro Ser Thr Pro Val Gly Ser Pro Gln Gly Leu Ala Gly Thr Ser Gln
        355                 360                 365
Trp Pro Arg Ala Gly Ala Pro Gly Ala Leu Ser Pro Ser Tyr Asp Gly
    370                 375                 380
Gly Leu His Gly Leu Gln Ser Lys Ile Glu Asp His Leu Asp Glu Ala
385                 390                 395                 400
Ile His Val Leu Arg Ser His Ala Val Gly Thr Ala Gly Asp Met His
                405                 410                 415
Thr Leu Leu Pro Gly His Gly Ala Leu Ala Ser Gly Phe Thr Gly Pro
            420                 425                 430
Met Ser Leu Gly Gly Arg His Ala Gly Leu Val Gly Gly Ser His Pro
        435                 440                 445
Glu Asp Gly Leu Ala Gly Ser Thr Ser Leu Met His Asn His Ala Ala
    450                 455                 460
Leu Pro Ser Gln Pro Gly Thr Leu Pro Asp Leu Ser Arg Pro Pro Asp
465                 470                 475                 480
Ser Tyr Ser Gly Leu Gly Arg Ala Gly Ala Thr Ala Ala Ser Glu
                485                 490                 495
Ile Lys Arg Glu Glu Lys Glu Asp Glu Glu Asn Thr Ser Ala Ala Asp
            500                 505                 510
His Ser Glu Glu Glu Lys Lys Glu Leu Lys Ala Pro Arg Ala Arg Thr
        515                 520                 525
Ser Pro Asp Glu Asp Glu Asp Leu Leu Pro Pro Glu Gln Lys Ala
    530                 535                 540
Glu Arg Glu Lys Glu Arg Arg Val Ala Asn Asn Ala Arg Glu Arg Leu
545                 550                 555                 560
Arg Val Arg Asp Ile Asn Glu Ala Phe Lys Glu Leu Gly Arg Met Cys
                565                 570                 575
Gln Leu His Leu Asn Ser Glu Lys Pro Gln Thr Lys Leu Leu Ile Leu
            580                 585                 590
His Gln Ala Val Ser Val Ile Leu Asn Leu Glu Gln Gln Val Arg Glu
        595                 600                 605
Arg Asn Leu Asn Pro Lys Ala Ala Cys Leu Lys Arg Arg Glu Glu Glu
    610                 615                 620
Lys Val Ser Gly Val Val Gly Asp Pro Gln Met Val Leu Ser Ala Pro
625                 630                 635                 640
His Pro Gly Leu Ser Glu Ala His Asn Pro Ala Gly His Met
                645                 650

<210> SEQ ID NO 10
```

```
<211> LENGTH: 157
<212> TYPE: PRT
<213> ORGANISM: Homo sapiens
<300> PUBLICATION INFORMATION:
<308> DATABASE ACCESSION NUMBER: SWISS-PROT/A0PJ75
<309> DATABASE ENTRY DATE: 2007-01-09
<313> RELEVANT RESIDUES IN SEQ ID NO: (1)..(157)

<400> SEQUENCE: 10

Gly Thr Gln Arg Ser Glu Pro Ala Leu Ala Pro Ala Asp Phe Val Ala
1               5                   10                  15

Pro Leu Ala Pro Leu Pro Ile Pro Ser Asn Leu Phe Val Pro Thr Pro
            20                  25                  30

Asp Ala Glu Glu Pro Gln Leu Pro Asp Gly Thr Gly Arg Glu Gly Pro
        35                  40                  45

Ala Ala Ala Arg Gly Leu Ala Asn Pro Glu Pro Ala Pro Glu Pro Lys
    50                  55                  60

Val Leu Ser Ser Ala Ala Ser Leu Pro Gly Ser Glu Leu Pro Ser Ser
65                  70                  75                  80

Arg Pro Glu Gly Ser Gln Gly Gly Glu Leu Ser Arg Cys Ser Ser Met
                85                  90                  95

Ser Ser Leu Ser Arg Glu Val Ser Gln His Phe Asn Gln Ala Pro Gly
            100                 105                 110

Asp Leu Pro Ala Ala Gly Gly Pro Ser Gly Ala Met Pro Phe Tyr
        115                 120                 125

Asn Pro Ala Gln Leu Ala Gln Ala Cys Ala Thr Ser Gly Ser Ser Arg
    130                 135                 140

Leu Gly Arg Ile Gly Gln Arg Lys His Leu Val Leu Asn
145                 150                 155

<210> SEQ ID NO 11
<211> LENGTH: 215
<212> TYPE: PRT
<213> ORGANISM: Homo sapiens
<300> PUBLICATION INFORMATION:
<308> DATABASE ACCESSION NUMBER: SWISS-PROT/P09429
<309> DATABASE ENTRY DATE: 1989-07-01
<313> RELEVANT RESIDUES IN SEQ ID NO: (1)..(214)

<400> SEQUENCE: 11

Met Gly Lys Gly Asp Pro Lys Lys Pro Arg Gly Lys Met Ser Ser Tyr
1               5                   10                  15

Ala Phe Phe Val Gln Thr Cys Arg Glu Glu His Lys Lys Lys His Pro
            20                  25                  30

Asp Ala Ser Val Asn Phe Ser Glu Phe Ser Lys Lys Cys Ser Glu Arg
        35                  40                  45

Trp Lys Thr Met Ser Ala Lys Glu Lys Gly Lys Phe Glu Asp Met Ala
    50                  55                  60

Lys Ala Asp Lys Ala Arg Tyr Glu Arg Glu Met Lys Thr Tyr Ile Pro
65                  70                  75                  80

Pro Lys Gly Glu Thr Lys Lys Lys Phe Lys Asp Pro Asn Ala Pro Lys
                85                  90                  95

Arg Pro Pro Ser Ala Phe Phe Leu Phe Cys Ser Glu Tyr Arg Pro Lys
            100                 105                 110

Ile Lys Gly Glu His Pro Gly Leu Ser Ile Gly Asp Val Ala Lys Lys
        115                 120                 125

Leu Gly Glu Met Trp Asn Asn Thr Ala Ala Asp Asp Lys Gln Pro Tyr
    130                 135                 140

Glu Lys Lys Ala Ala Lys Leu Lys Glu Lys Tyr Glu Lys Asp Ile Ala
```

-continued

```
            145                 150                 155                 160
Ala Tyr Arg Ala Lys Gly Lys Pro Asp Ala Lys Lys Gly Val Val
                165                 170                 175

Lys Ala Glu Lys Ser Lys Lys Lys Glu Glu Glu Asp Glu Glu
            180                 185                 190

Asp Glu Glu Asp Glu Glu Glu Glu Asp Glu Glu Asp Glu Asp Glu
        195                 200                 205

Glu Glu Asp Asp Asp Asp Glu
    210                 215

<210> SEQ ID NO 12
<211> LENGTH: 347
<212> TYPE: PRT
<213> ORGANISM: Homo sapiens
<300> PUBLICATION INFORMATION:
<308> DATABASE ACCESSION NUMBER: SWISS-PROT/Q6ZV59
<309> DATABASE ENTRY DATE: 2007-07-24
<313> RELEVANT RESIDUES IN SEQ ID NO: (1)..(347)

<400> SEQUENCE: 12

Met Pro Gln Ala Glu Leu Gly Ile Gln Val Cys Thr Cys Arg Leu Arg
1               5                   10                  15

Gly Ser Val Ser Arg Cys Cys Ser His Arg Glu Phe Arg Arg Gln Pro
            20                  25                  30

Ser Pro Cys Ala Ala Gly Ile Gly Leu Leu His Leu Gly Ser Thr Ala
        35                  40                  45

Ser Arg Gln Val Lys Pro Pro Arg Leu Pro Pro Pro Trp Gly Arg
    50                  55                  60

Ser Gly Glu Lys Leu Pro Phe Thr Pro Phe Pro Gly Cys Ser Leu Ser
65                  70                  75                  80

Arg Trp His Ala Ser Pro Gln Thr Gln Val Ala Phe Gly Pro Arg Trp
                85                  90                  95

Val Ser Leu Leu Pro Leu Pro His Thr Pro Ser Gly His Trp Asp Pro
            100                 105                 110

Cys Pro Ser Asp Val Leu Gly Ser Arg Ser Gly Ala Ser His Cys Gly
        115                 120                 125

Lys Arg Pro Gly Ala Trp Pro Glu Arg Gln Pro Arg Ala Gly Leu Ser
    130                 135                 140

Pro Glu Ser Trp Ser Arg Ala Arg Glu Ala Pro Ile Pro Pro Arg Pro
145                 150                 155                 160

Ala Ala Leu Ser Ala Val Ser Ser Ile Cys Ser Ser Phe His Pro Gln
                165                 170                 175

Leu Cys Val Pro Val Ile Pro Pro Phe Ser Lys Ser Pro Val Pro Ile
            180                 185                 190

Pro Ser Val Pro Thr His Ser Cys Ser Pro Lys Lys Ile Ser Tyr Arg
        195                 200                 205

Cys Ile Tyr Asn Leu Trp Ile Arg Gly Leu Ser Ile Tyr Tyr Trp
    210                 215                 220

Leu Ile Ile Ile Asn Tyr Val Asn Leu Pro Val Cys Leu Leu Arg
225                 230                 235                 240

Trp Val Ser Glu Glu Thr Leu Gly Glu Glu Asp Ala Leu Ala Ser Arg
                245                 250                 255

Phe Ser Pro Pro Thr Pro Val Leu Ser Gly Arg Gln Trp Ser Gly Ala
            260                 265                 270

Thr Gly Trp Ala Pro Phe Ser Leu Pro Pro Ser Pro Cys Pro Phe Cys
        275                 280                 285
```

-continued

Arg Pro Leu Arg Gly Ala Val Cys Leu Ser Leu Ser Leu Leu Pro Leu
        290                 295                 300

Leu Arg His Trp Leu Pro Gln Ser Glu Gln Pro Ala Gly Gly Arg Arg
305                 310                 315                 320

Ser Cys Val Gly His Cys Leu Leu Gln Cys Cys Arg Arg Arg Ala Glu
                325                 330                 335

Ala Pro Pro Gly Gly Phe His Leu Thr Gln Pro
                340                 345

<210> SEQ ID NO 13
<211> LENGTH: 552
<212> TYPE: PRT
<213> ORGANISM: Homo sapiens
<300> PUBLICATION INFORMATION:
<308> DATABASE ACCESSION NUMBER: SWISS-PROT/Q9H0X4
<309> DATABASE ENTRY DATE: 2006-09-05
<313> RELEVANT RESIDUES IN SEQ ID NO: (1)..(552)

<400> SEQUENCE: 13

Met Leu Asp His Lys Asp Leu Glu Ala Glu Ile His Pro Leu Lys Asn
1               5                   10                  15

Glu Glu Arg Lys Ser Gln Glu Asn Leu Gly Asn Pro Ser Lys Asn Glu
            20                  25                  30

Asp Asn Val Lys Ser Ala Pro Pro Gln Ser Arg Leu Ser Arg Cys Arg
        35                  40                  45

Ala Ala Ala Phe Phe Leu Ser Leu Phe Leu Cys Leu Phe Val Val Phe
    50                  55                  60

Val Val Ser Phe Val Ile Pro Cys Pro Asp Arg Pro Ala Ser Gln Arg
65                  70                  75                  80

Met Trp Arg Ile Asp Tyr Ser Ala Ala Val Ile Tyr Asp Phe Leu Ala
                85                  90                  95

Val Asp Asp Ile Asn Gly Asp Arg Ile Gln Asp Val Leu Phe Leu Tyr
            100                 105                 110

Lys Asn Thr Asn Ser Ser Asn Asn Phe Ser Arg Ser Cys Val Asp Glu
        115                 120                 125

Gly Phe Ser Ser Pro Cys Thr Phe Ala Ala Ala Val Ser Gly Ala Asn
    130                 135                 140

Gly Ser Thr Leu Trp Glu Arg Pro Val Ala Gln Asp Val Ala Leu Val
145                 150                 155                 160

Glu Cys Ala Val Pro Gln Pro Arg Gly Ser Glu Ala Pro Ser Ala Cys
                165                 170                 175

Ile Leu Val Gly Arg Pro Ser Ser Phe Ile Ala Val Asn Leu Phe Thr
            180                 185                 190

Gly Glu Thr Leu Trp Asn His Ser Ser Ser Phe Ser Gly Asn Ala Ser
        195                 200                 205

Ile Leu Ser Pro Leu Leu Gln Val Pro Asp Val Asp Gly Asp Gly Ala
    210                 215                 220

Pro Asp Leu Leu Val Leu Thr Gln Glu Arg Glu Glu Val Ser Gly His
225                 230                 235                 240

Leu Tyr Ser Gly Ser Thr Gly His Gln Ile Gly Leu Arg Gly Ser Leu
                245                 250                 255

Gly Val Asp Gly Glu Ser Gly Phe Leu Leu His Val Thr Arg Thr Gly
            260                 265                 270

Ala His Tyr Ile Leu Phe Pro Cys Ala Ser Ser Leu Cys Gly Cys Ser
        275                 280                 285

Val Lys Gly Leu Tyr Glu Lys Val Thr Gly Ser Gly Gly Pro Phe Lys
    290                 295                 300

```
Ser Asp Pro His Trp Glu Ser Met Leu Asn Ala Thr Thr Arg Arg Met
305                 310                 315                 320

Leu Ser His Ser Ser Gly Ala Val Arg Tyr Leu Met His Val Pro Gly
            325                 330                 335

Asn Ala Gly Ala Asp Val Leu Leu Val Gly Ser Glu Ala Phe Val Leu
                340                 345                 350

Leu Asp Gly Gln Glu Leu Thr Pro Arg Trp Thr Pro Lys Ala Ala His
            355                 360                 365

Val Leu Arg Lys Pro Ile Phe Gly Arg Tyr Lys Pro Asp Thr Leu Ala
        370                 375                 380

Val Ala Val Glu Asn Gly Thr Gly Thr Asp Arg Gln Ile Leu Phe Leu
385                 390                 395                 400

Asp Leu Gly Thr Gly Ala Val Leu Cys Ser Leu Ala Leu Pro Ser Leu
                405                 410                 415

Pro Gly Gly Pro Leu Ser Ala Ser Leu Pro Thr Ala Asp His Arg Ser
            420                 425                 430

Ala Phe Phe Phe Trp Gly Leu His Glu Leu Gly Ser Thr Ser Glu Thr
        435                 440                 445

Glu Thr Gly Glu Ala Arg His Ser Leu Tyr Met Phe His Pro Thr Leu
450                 455                 460

Pro Arg Val Leu Leu Glu Leu Ala Asn Val Ser Thr His Ile Val Ala
465                 470                 475                 480

Phe Asp Ala Val Leu Phe Glu Pro Ser Arg His Ala Ala Tyr Ile Leu
                485                 490                 495

Leu Thr Gly Pro Ala Asp Ser Glu Ala Pro Gly Leu Val Ser Val Ile
            500                 505                 510

Lys His Lys Val Arg Asp Leu Val Pro Ser Ser Arg Val Val Arg Leu
        515                 520                 525

Gly Glu Gly Gly Pro Asp Ser Asp Gln Ala Ile Arg Asp Arg Phe Ser
530                 535                 540

Arg Leu Arg Tyr Gln Ser Glu Ala
545                 550
```

<210> SEQ ID NO 14
<211> LENGTH: 258
<212> TYPE: PRT
<213> ORGANISM: Homo sapiens
<300> PUBLICATION INFORMATION:
<308> DATABASE ACCESSION NUMBER: SWISS-PROT/O95721
<309> DATABASE ENTRY DATE: 2000-05-30
<313> RELEVANT RESIDUES IN SEQ ID NO: (1)..(258)

<400> SEQUENCE: 14

```
Met Ser Ala Tyr Pro Lys Ser Tyr Asn Pro Phe Asp Asp Gly Glu
1               5                   10                  15

Asp Glu Gly Ala Arg Pro Ala Pro Trp Arg Asp Ala Arg Asp Leu Pro
            20                  25                  30

Asp Gly Pro Asp Ala Pro Ala Asp Arg Gln Gln Tyr Leu Arg Gln Glu
        35                  40                  45

Val Leu Arg Arg Ala Glu Ala Thr Ala Ala Ser Thr Ser Arg Ser Leu
    50                  55                  60

Ala Leu Met Tyr Glu Ser Glu Lys Val Gly Val Ala Ser Glu Glu
65                  70                  75                  80

Leu Ala Arg Gln Arg Gly Val Leu Glu Arg Thr Glu Lys Met Val Asp
            85                  90                  95

Lys Met Asp Gln Asp Leu Lys Ile Ser Gln Lys His Ile Asn Ser Ile
```

```
                    100                 105                 110
Lys Ser Val Phe Gly Gly Leu Val Asn Tyr Phe Lys Ser Lys Pro Val
            115                 120                 125

Glu Thr Pro Pro Glu Gln Asn Gly Thr Leu Thr Ser Gln Pro Asn Asn
130                 135                 140

Arg Leu Lys Glu Ala Ile Ser Thr Ser Lys Glu Gln Glu Ala Lys Tyr
145                 150                 155                 160

Gln Ala Ser His Pro Asn Leu Arg Lys Leu Asp Asp Thr Asp Pro Val
            165                 170                 175

Pro Arg Gly Ala Gly Ser Ala Met Ser Thr Asp Ala Tyr Pro Lys Asn
            180                 185                 190

Pro His Leu Arg Ala Tyr His Gln Lys Ile Asp Ser Asn Leu Asp Glu
            195                 200                 205

Leu Ser Met Gly Leu Gly Arg Leu Lys Asp Ile Ala Leu Gly Met Gln
            210                 215                 220

Thr Glu Ile Glu Glu Gln Asp Asp Ile Leu Asp Arg Leu Thr Thr Lys
225                 230                 235                 240

Val Asp Lys Leu Asp Val Asn Ile Lys Ser Thr Glu Arg Lys Val Arg
            245                 250                 255

Gln Leu

<210> SEQ ID NO 15
<211> LENGTH: 288
<212> TYPE: PRT
<213> ORGANISM: Homo sapiens
<300> PUBLICATION INFORMATION:
<308> DATABASE ACCESSION NUMBER: SWISS-PROT/P27105
<309> DATABASE ENTRY DATE: 1992-08-01
<313> RELEVANT RESIDUES IN SEQ ID NO: (1)..(288)

<400> SEQUENCE: 15

Met Ala Glu Lys Arg His Thr Arg Asp Ser Glu Ala Gln Arg Leu Pro
1               5                   10                  15

Asp Ser Phe Lys Asp Ser Pro Ser Lys Gly Leu Gly Pro Cys Gly Trp
            20                  25                  30

Ile Leu Val Ala Phe Ser Phe Leu Phe Thr Val Ile Thr Phe Pro Ile
            35                  40                  45

Ser Ile Trp Met Cys Ile Lys Ile Ile Lys Glu Tyr Glu Arg Ala Ile
        50                  55                  60

Ile Phe Arg Leu Gly Arg Ile Leu Gln Gly Gly Ala Lys Gly Pro Gly
65                  70                  75                  80

Leu Phe Phe Ile Leu Pro Cys Thr Asp Ser Phe Ile Lys Val Asp Met
            85                  90                  95

Arg Thr Ile Ser Phe Asp Ile Pro Pro Gln Glu Ile Leu Thr Lys Asp
            100                 105                 110

Ser Val Thr Ile Ser Val Asp Gly Val Val Tyr Tyr Arg Val Gln Asn
            115                 120                 125

Ala Thr Leu Ala Val Ala Asn Ile Thr Asn Ala Asp Ser Ala Thr Arg
130                 135                 140

Leu Leu Ala Gln Thr Thr Leu Arg Asn Val Leu Gly Thr Lys Asn Leu
145                 150                 155                 160

Ser Gln Ile Leu Ser Asp Arg Glu Glu Ile Ala His Asn Met Gln Ser
            165                 170                 175

Thr Leu Asp Asp Ala Thr Asp Ala Trp Gly Ile Lys Val Glu Arg Val
            180                 185                 190

Glu Ile Lys Asp Val Lys Leu Pro Val Gln Leu Gln Arg Ala Met Ala
```

```
                    195                 200                 205
Ala Glu Ala Glu Ala Ser Arg Glu Ala Arg Ala Lys Val Ile Ala Ala
    210                 215                 220

Glu Gly Glu Met Asn Ala Ser Arg Ala Leu Lys Glu Ala Ser Met Val
225                 230                 235                 240

Ile Thr Glu Ser Pro Ala Ala Leu Gln Leu Arg Tyr Leu Gln Thr Leu
                    245                 250                 255

Thr Thr Ile Ala Ala Glu Lys Asn Ser Thr Ile Val Phe Pro Leu Pro
                260                 265                 270

Ile Asp Met Leu Gln Gly Ile Ile Gly Ala Lys His Ser His Leu Gly
            275                 280                 285

<210> SEQ ID NO 16
<211> LENGTH: 290
<212> TYPE: PRT
<213> ORGANISM: Homo sapiens
<300> PUBLICATION INFORMATION:
<308> DATABASE ACCESSION NUMBER: SWISS-PROT/Q14135
<309> DATABASE ENTRY DATE: 1997-11-01
<313> RELEVANT RESIDUES IN SEQ ID NO: (1)..(290)

<400> SEQUENCE: 16

Met Glu Thr Pro Leu Asp Val Leu Ser Arg Ala Ala Ser Leu Val His
1               5                   10                  15

Ala Asp Asp Glu Lys Arg Glu Ala Ala Leu Arg Gly Glu Pro Arg Met
            20                  25                  30

Gln Thr Leu Pro Val Ala Ser Ala Leu Ser Ser His Arg Thr Gly Pro
        35                  40                  45

Pro Pro Ile Ser Pro Ser Lys Arg Lys Phe Ser Met Glu Pro Gly Asp
    50                  55                  60

Glu Asp Leu Asp Cys Asp Asn Asp His Val Ser Lys Met Ser Arg Ile
65                  70                  75                  80

Phe Asn Pro His Leu Asn Lys Thr Ala Asn Gly Asp Cys Arg Arg Asp
                85                  90                  95

Pro Arg Glu Arg Ser Arg Ser Pro Ile Glu Arg Ala Val Ala Pro Thr
            100                 105                 110

Met Ser Leu His Gly Ser His Leu Tyr Thr Ser Leu Pro Ser Leu Gly
        115                 120                 125

Leu Glu Gln Pro Leu Ala Leu Thr Lys Asn Ser Leu Asp Ala Ser Arg
    130                 135                 140

Pro Ala Gly Leu Ser Pro Thr Leu Thr Pro Gly Glu Arg Gln Gln Asn
145                 150                 155                 160

Arg Pro Ser Val Ile Thr Cys Ala Ser Ala Gly Ala Arg Asn Cys Asn
                165                 170                 175

Leu Ser His Cys Pro Ile Ala His Ser Gly Cys Ala Ala Pro Gly Pro
            180                 185                 190

Ala Ser Tyr Arg Arg Pro Pro Ser Ala Ala Thr Thr Cys Asp Pro Val
        195                 200                 205

Val Glu Glu His Phe Arg Arg Ser Leu Gly Lys Asn Tyr Lys Glu Pro
    210                 215                 220

Glu Pro Ala Pro Asn Ser Val Ser Ile Thr Gly Ser Val Asp Asp His
225                 230                 235                 240

Phe Ala Lys Ala Leu Gly Asp Thr Trp Leu Gln Ile Lys Ala Ala Lys
                245                 250                 255

Asp Gly Ala Ser Ser Ser Pro Glu Ser Ala Ser Arg Arg Gly Gln Pro
            260                 265                 270
```

-continued

```
Ala Ser Pro Ser Ala His Met Val Ser His Ser His Ser Pro Ser Val
        275                 280                 285

Val Ser
    290

<210> SEQ ID NO 17
<211> LENGTH: 835
<212> TYPE: PRT
<213> ORGANISM: Homo sapiens
<300> PUBLICATION INFORMATION:
<308> DATABASE ACCESSION NUMBER: SWISS-PROT/Q13263
<309> DATABASE ENTRY DATE: 1998-07-15
<313> RELEVANT RESIDUES IN SEQ ID NO: (1)..(835)

<400> SEQUENCE: 17

Met Ala Ser Ala Ala Ala Ser Ala Ala Ala Ser Ala Ala Ser Ala Ala
1               5                   10                  15

Ser Gly Ser Pro Gly Pro Gly Glu Gly Ser Ala Gly Gly Glu Lys Arg
            20                  25                  30

Ser Thr Ala Pro Ser Ala Ala Ala Ser Ala Ser Ala Ser Ala Ala Ala
        35                  40                  45

Ser Ser Pro Ala Gly Gly Gly Ala Glu Ala Leu Glu Leu Leu Glu His
    50                  55                  60

Cys Gly Val Cys Arg Glu Arg Leu Arg Pro Glu Arg Glu Pro Arg Leu
65                  70                  75                  80

Leu Pro Cys Leu His Ser Ala Cys Ser Ala Cys Leu Gly Pro Ala Ala
                85                  90                  95

Pro Ala Ala Ala Asn Ser Ser Gly Asp Gly Ala Ala Gly Asp Gly
            100                 105                 110

Thr Val Val Asp Cys Pro Val Cys Lys Gln Gln Cys Phe Ser Lys Asp
        115                 120                 125

Ile Val Glu Asn Tyr Phe Met Arg Asp Ser Gly Ser Lys Ala Ala Thr
    130                 135                 140

Asp Ala Gln Asp Ala Asn Gln Cys Cys Thr Ser Cys Glu Asp Asn Ala
145                 150                 155                 160

Pro Ala Thr Ser Tyr Cys Val Glu Cys Ser Glu Pro Leu Cys Glu Thr
                165                 170                 175

Cys Val Glu Ala His Gln Arg Val Lys Tyr Thr Lys Asp His Thr Val
            180                 185                 190

Arg Ser Thr Gly Pro Ala Lys Ser Arg Asp Gly Glu Arg Thr Val Tyr
        195                 200                 205

Cys Asn Val His Lys His Glu Pro Leu Val Leu Phe Cys Glu Ser Cys
    210                 215                 220

Asp Thr Leu Thr Cys Arg Asp Cys Gln Leu Asn Ala His Lys Asp His
225                 230                 235                 240

Gln Tyr Gln Phe Leu Glu Asp Ala Val Arg Asn Gln Arg Lys Leu Leu
                245                 250                 255

Ala Ser Leu Val Lys Arg Leu Gly Asp Lys His Ala Thr Leu Gln Lys
            260                 265                 270

Ser Thr Lys Glu Val Arg Ser Ser Ile Arg Gln Val Ser Asp Val Gln
        275                 280                 285

Lys Arg Val Gln Val Asp Val Lys Met Ala Ile Leu Gln Ile Met Lys
    290                 295                 300

Glu Leu Asn Lys Arg Gly Arg Val Leu Val Asn Asp Ala Gln Lys Val
305                 310                 315                 320

Thr Glu Gly Gln Gln Glu Arg Leu Glu Arg Gln His Trp Thr Met Thr
                325                 330                 335
```

-continued

```
Lys Ile Gln Lys His Gln Glu His Ile Leu Arg Phe Ala Ser Trp Ala
            340                 345                 350
Leu Glu Ser Asp Asn Asn Thr Ala Leu Leu Ser Lys Lys Leu Ile
            355                 360             365
Tyr Phe Gln Leu His Arg Ala Leu Lys Met Ile Val Asp Pro Val Glu
            370                 375                 380
Pro His Gly Glu Met Lys Phe Gln Trp Asp Leu Asn Ala Trp Thr Lys
385                 390                 395                 400
Ser Ala Glu Ala Phe Gly Lys Ile Val Ala Glu Arg Pro Gly Thr Asn
                    405                 410                 415
Ser Thr Gly Pro Ala Pro Met Ala Pro Pro Arg Ala Pro Gly Pro Leu
                420                 425                 430
Ser Lys Gln Gly Ser Gly Ser Ser Gln Pro Met Glu Val Gln Glu Gly
            435                 440                 445
Tyr Gly Phe Gly Ser Gly Asp Asp Pro Tyr Ser Ser Ala Glu Pro His
            450                 455                 460
Val Ser Gly Val Lys Arg Ser Arg Ser Gly Glu Gly Glu Val Ser Gly
465                 470                 475                 480
Leu Met Arg Lys Val Pro Arg Val Ser Leu Glu Arg Leu Asp Leu Asp
                    485                 490                 495
Leu Thr Ala Asp Ser Gln Pro Pro Val Phe Lys Val Phe Pro Gly Ser
                500                 505                 510
Thr Thr Glu Asp Tyr Asn Leu Ile Val Ile Glu Arg Gly Ala Ala Ala
            515                 520                 525
Ala Ala Thr Gly Gln Pro Gly Thr Ala Pro Ala Gly Thr Pro Gly Ala
            530                 535                 540
Pro Pro Leu Ala Gly Met Ala Ile Val Lys Glu Glu Thr Glu Ala
545                 550                 555                 560
Ala Ile Gly Ala Pro Pro Thr Ala Thr Glu Gly Pro Glu Thr Lys Pro
                    565                 570                 575
Val Leu Met Ala Leu Ala Glu Gly Pro Gly Ala Glu Gly Pro Arg Leu
                580                 585                 590
Ala Ser Pro Ser Gly Ser Thr Ser Ser Gly Leu Glu Val Val Ala Pro
            595                 600                 605
Glu Gly Thr Ser Ala Pro Gly Gly Pro Gly Thr Leu Asp Asp Ser
            610                 615                 620
Ala Thr Ile Cys Arg Val Cys Gln Lys Pro Gly Asp Leu Val Met Cys
625                 630                 635                 640
Asn Gln Cys Glu Phe Cys Phe His Leu Asp Cys His Leu Pro Ala Leu
                    645                 650                 655
Gln Asp Val Pro Gly Glu Glu Trp Ser Cys Ser Leu Cys His Val Leu
                660                 665                 670
Pro Asp Leu Lys Glu Glu Asp Gly Ser Leu Ser Leu Asp Gly Ala Asp
            675                 680                 685
Ser Thr Gly Val Val Ala Lys Leu Ser Pro Ala Asn Gln Arg Lys Cys
            690                 695                 700
Glu Arg Val Leu Leu Ala Leu Phe Cys His Glu Pro Cys Arg Pro Leu
705                 710                 715                 720
His Gln Leu Ala Thr Asp Ser Thr Phe Ser Leu Asp Gln Pro Gly Gly
                    725                 730                 735
Thr Leu Asp Leu Thr Leu Ile Arg Ala Arg Leu Gln Glu Lys Leu Ser
                740                 745                 750
Pro Pro Tyr Ser Ser Pro Gln Glu Phe Ala Gln Asp Val Gly Arg Met
```

```
                   755                 760                 765
Phe Lys Gln Phe Asn Lys Leu Thr Glu Asp Lys Ala Asp Val Gln Ser
        770                 775                 780

Ile Ile Gly Leu Gln Arg Phe Phe Glu Thr Arg Met Asn Glu Ala Phe
785                 790                 795                 800

Gly Asp Thr Lys Phe Ser Ala Val Leu Val Glu Pro Pro Met Ser
                805                 810                 815

Leu Pro Gly Ala Gly Leu Ser Ser Gln Glu Leu Ser Gly Pro Gly
            820                 825                 830

Asp Gly Pro
        835

<210> SEQ ID NO 18
<211> LENGTH: 420
<212> TYPE: PRT
<213> ORGANISM: Homo sapiens
<300> PUBLICATION INFORMATION:
<308> DATABASE ACCESSION NUMBER: SWISS-PROT/O14979
<309> DATABASE ENTRY DATE: 2007-05-15
<313> RELEVANT RESIDUES IN SEQ ID NO: (1)..(420)

<400> SEQUENCE: 18

Met Glu Val Pro Pro Arg Leu Ser His Val Pro Pro Leu Phe Pro
1               5                   10                  15

Ser Ala Pro Ala Thr Leu Ala Ser Arg Ser Leu Ser His Trp Arg Pro
            20                  25                  30

Arg Pro Pro Arg Gln Leu Ala Pro Leu Leu Pro Ser Leu Ala Pro Ser
        35                  40                  45

Ser Ala Arg Gln Gly Ala Arg Ala Gln Arg His Val Thr Ala Gln
    50                  55                  60

Gln Pro Ser Arg Leu Ala Gly Ala Ala Ile Lys Gly Gly Arg Arg
65                  70                  75                  80

Arg Arg Pro Asp Leu Phe Arg Arg His Phe Lys Ser Ser Ile Gln
                85                  90                  95

Arg Ser Ala Ala Ala Ala Ala Thr Arg Thr Ala Arg Gln His Pro
            100                 105                 110

Pro Ala Asp Ser Ser Val Thr Met Glu Asp Met Asn Glu Tyr Ser Asn
        115                 120                 125

Ile Glu Glu Phe Ala Glu Gly Ser Lys Ile Asn Ala Ser Lys Asn Gln
    130                 135                 140

Gln Asp Asp Gly Lys Met Phe Ile Gly Gly Leu Ser Trp Asp Thr Ser
145                 150                 155                 160

Lys Lys Asp Leu Thr Glu Tyr Leu Ser Arg Phe Gly Glu Val Val Asp
                165                 170                 175

Cys Thr Ile Lys Thr Asp Pro Val Thr Gly Arg Ser Arg Gly Phe Gly
            180                 185                 190

Phe Val Leu Phe Lys Asp Ala Ala Ser Val Asp Lys Val Leu Glu Leu
        195                 200                 205

Lys Glu His Lys Leu Asp Gly Lys Leu Ile Asp Pro Lys Arg Ala Lys
    210                 215                 220

Ala Leu Lys Gly Lys Glu Pro Pro Lys Lys Val Phe Val Gly Gly Leu
225                 230                 235                 240

Ser Pro Asp Thr Ser Glu Glu Gln Ile Lys Glu Tyr Phe Gly Ala Phe
                245                 250                 255

Gly Glu Ile Glu Asn Ile Glu Leu Pro Met Asp Thr Lys Thr Asn Glu
            260                 265                 270
```

```
Arg Arg Gly Phe Cys Phe Ile Thr Tyr Thr Asp Glu Glu Pro Val Lys
            275                 280                 285

Lys Leu Leu Glu Ser Arg Tyr His Gln Ile Gly Ser Gly Lys Cys Glu
    290                 295                 300

Ile Lys Val Ala Gln Pro Lys Glu Val Tyr Arg Gln Gln Gln Gln Gln
305                 310                 315                 320

Gln Lys Gly Gly Arg Gly Ala Ala Gly Gly Arg Gly Gly Thr Arg
                325                 330                 335

Gly Arg Gly Arg Gly Gln Gly Gln Asn Trp Asn Gln Gly Phe Asn Asn
                340                 345                 350

Tyr Tyr Asp Gln Gly Tyr Gly Asn Tyr Asn Ser Ala Tyr Gly Gly Asp
            355                 360                 365

Gln Asn Tyr Ser Gly Tyr Gly Gly Tyr Asp Tyr Thr Gly Tyr Asn Tyr
    370                 375                 380

Gly Asn Tyr Gly Tyr Gly Gln Gly Tyr Ala Asp Tyr Ser Gly Gln Gln
385                 390                 395                 400

Ser Thr Tyr Gly Lys Ala Ser Arg Gly Gly Gly Asn His Gln Asn Asn
                405                 410                 415

Tyr Gln Pro Tyr
            420

<210> SEQ ID NO 19
<211> LENGTH: 273
<212> TYPE: PRT
<213> ORGANISM: Homo sapiens

<400> SEQUENCE: 19

Met Gly Arg Ser Arg Ser Arg Ser Ser Arg Ser Lys His Thr Lys
1               5                   10                  15

Ser Ser Lys His Asn Lys Lys Arg Ser Arg Ser Arg Ser Arg Ser Arg
                20                  25                  30

Asp Lys Glu Arg Val Arg Lys Arg Ser Lys Ser Arg Glu Ser Lys Arg
            35                  40                  45

Asn Arg Arg Arg Glu Ser Arg Ser Arg Ser Arg Ser Thr Asn Thr Ala
50                  55                  60

Val Ser Arg Arg Glu Arg Asp Arg Glu Arg Ala Ser Ser Pro Pro Asp
65                  70                  75                  80

Arg Ile Asp Ile Phe Gly Arg Thr Val Ser Lys Arg Ser Ser Leu Asp
                85                  90                  95

Glu Lys Gln Lys Arg Glu Glu Glu Lys Lys Ala Gly Phe Glu Arg
            100                 105                 110

Gln Arg Lys Ile Arg Gln Gln Glu Ile Glu Glu Lys Leu Ile Glu Glu
        115                 120                 125

Glu Thr Ala Arg Arg Val Glu Glu Leu Val Ala Lys Arg Val Glu Glu
    130                 135                 140

Glu Leu Glu Lys Arg Lys Asp Glu Ile Glu Arg Glu Val Leu Arg Arg
145                 150                 155                 160

Val Glu Glu Ala Lys Arg Ile Met Glu Lys Gln Leu Leu Glu Glu Leu
                165                 170                 175

Glu Arg Gln Arg Gln Ala Glu Leu Ala Ala Gln Lys Ala Arg Glu Val
            180                 185                 190

Thr Leu Gly Arg Leu Glu Ser Arg Asp Ser Pro Trp Gln Asn Phe Gln
        195                 200                 205

Cys Trp Val Leu Pro Pro Ala Gln Phe Arg Lys Arg Trp Asn Thr Asp
    210                 215                 220
```

-continued

Tyr Leu Ile Pro Phe Ser Ser Lys Leu Asn Ile Ala Ala Lys Val Asn
225                 230                 235                 240

Phe Leu Ala Tyr Ser Glu Val Leu Thr Asp Asn Leu Lys Val Gly Ser
            245                 250                 255

Phe Tyr Lys Thr Tyr Ser Arg Ile Leu Phe Asp Leu Met Glu Leu Ala
            260                 265                 270

Ile

<210> SEQ ID NO 20
<211> LENGTH: 682
<212> TYPE: PRT
<213> ORGANISM: Rattus norvegicus

<400> SEQUENCE: 20

Met Ala Leu Arg Thr Gly Pro Arg Ser Arg Pro Ala Gly Gly Pro
1               5                   10                  15

Ala Pro His Pro Gly Arg Arg Gly Gly Asp Pro Pro Asp Gly Asp
                20                  25                  30

Gly Arg Gly Ala Gly Tyr Pro Gly Pro Thr Glu Ala Pro Ser Ala Leu
            35                  40                  45

Pro Lys Ser Arg His Arg Ile Lys Lys Arg Arg Tyr Glu Arg
50                  55                  60

Leu Ala Thr Ser Gln Leu Ser Leu Trp Cys Thr Ala Pro Val Lys
65                  70                  75                  80

Leu Pro Thr Trp His Cys Pro Arg Ser Gly Ser Arg Pro Pro Ala Arg
                85                  90                  95

Ala Asp Gly Arg Leu Ala Pro Glu Ala Arg Ala Pro Arg Gly Ser Pro
            100                 105                 110

Pro Pro Pro His Arg Ala Pro Ala Glu Ala Arg Arg Ala Gly Asn
            115                 120                 125

Arg Gly Pro Gly Gly Ala Pro Gly Gly Gly Thr Ala Asp Ala Glu Glu
130                 135                 140

Asn Pro Glu Pro Arg Glu Pro Thr Pro Arg Arg Gly Lys Gly Glu
145                 150                 155                 160

Asp Glu Ala Gly Gly Lys Pro Arg Ala Gly Asp Pro Gly Pro Arg
                165                 170                 175

Gly Arg Ala Pro Ala Ala Pro Val Pro Phe Arg Leu Pro Ala Thr
            180                 185                 190

Ala Gly Ser Asp Asp Arg Phe Ala Arg Gln Asp Arg Tyr Gly Pro Pro
            195                 200                 205

Pro Glu Phe Pro Leu Ala Ser Pro Cys Pro Gly Ile Val His His Leu
210                 215                 220

Ser Gly Pro Asn Ala Tyr Ala Arg Ala Pro Pro Arg Arg Gly Gly
225                 230                 235                 240

Arg Asp Gly Pro Val Val Arg Pro Arg Thr Gly Glu Ala Ser Gly
                245                 250                 255

Ser His Leu Gly Ala Pro Gly Asn Gly Ala Leu His Leu His Cys Ala
            260                 265                 270

Thr Ala Ala Phe Gly Arg Ala Pro Asp Ser Arg Thr Leu Leu Phe Asn
            275                 280                 285

Phe Pro Leu Arg Tyr Leu Leu Ala Ile Gly Leu Val Pro Val Phe Ser
            290                 295                 300

Leu Arg Trp Ser Leu Pro Pro Ala Leu Gly Cys Ile Pro Lys Gln Pro
305                 310                 315                 320

Asp Ser Gly Lys Thr Arg Ala Arg Arg Ala Gly Gly Arg Tyr Arg Pro

```
                   325                 330                 335
His Thr Val His Gly Leu Gly Leu Asp Gln Lys Asp Leu Gly Pro Pro
            340                 345                 350

Arg Ala Ala Pro Gly Ser Gly Ser Arg Val Ala Thr Ser Asp Leu
        355                 360                 365

Arg Ser Arg Ser Arg Gly Gly Glu Gly Gly Val Gly Ala Arg Gly
    370                 375                 380

Arg Arg Lys Glu Arg Gly Glu Arg Glu Arg Arg Asp Asp
385                 390                 395                 400

Gly Ala Arg Ala Pro Gly Glu Pro Arg Pro Glu Pro Ala Thr Ser Pro
            405                 410                 415

Ser Pro Ala Gly Ser His Ile Pro Gly Ala Ser Arg Val Arg Ala Arg
        420                 425                 430

Thr Pro Arg Arg Pro Ala Gly Arg Arg Ser Gly Arg Pro Pro Val
        435                 440                 445

Glu Gly Ala Gly Glu Arg Val Ser Arg Ser Ala Pro Ala Gly Ala
        450                 455                 460

Gly Asp Pro Pro Gly Val Phe Lys Pro Pro Arg Arg Asn Ala Arg Ala
465                 470                 475                 480

Arg Tyr Pro Asp Arg Ser Gly Ala Asp Thr Arg Gly Pro Glu Gly Ala
            485                 490                 495

Ala Gly Arg Ala Ser Pro Pro Ala Ala Pro Ala His Thr Pro Pro
        500                 505                 510

His Ala Ala Glu Pro Pro Arg His Arg Gln Cys Arg Arg Ala Ala Ala
            515                 520                 525

Gly Glu Glu Arg Gln Ala Pro Arg Gly Glu Arg Ala Arg Pro Gly His
        530                 535                 540

Arg Pro Gly Arg Asp His Val Pro Pro Val His Thr Arg Ser Arg
545                 550                 555                 560

Ser Arg Ser Gly Lys Arg Gln Asn Ala Leu Gly Leu Pro Thr Ala Ala
            565                 570                 575

Ala Glu Ala Glu Ala Gly Ala Arg Arg Arg Gly Lys Ser Glu Lys
        580                 585                 590

Thr Glu Glu Val Pro Arg Arg Thr Arg Pro Asp Thr Leu Pro Pro His
            595                 600                 605

Thr Cys Pro Glu Thr Pro Ala Pro Pro Ala Gly His Gly Thr Arg His
        610                 615                 620

Asp Ala Arg Thr Pro Asp Thr Gly Thr His Pro Gly Thr Arg Leu Pro
625                 630                 635                 640

Ala Arg Arg Arg Asn Thr His Thr Gly Pro Arg Gly Asp Gly Thr Thr
            645                 650                 655

Thr Pro Pro Arg Pro Ser Pro Leu Met Ile Leu Pro Gln Val His Leu
        660                 665                 670

Arg Lys Pro Cys Tyr Asp Phe Tyr Phe Leu
        675                 680

<210> SEQ ID NO 21
<211> LENGTH: 2717
<212> TYPE: PRT
<213> ORGANISM: Homo sapiens
<300> PUBLICATION INFORMATION:
<308> DATABASE ACCESSION NUMBER: SWISS-PROT/P15822
<309> DATABASE ENTRY DATE: 1990-04-01
<313> RELEVANT RESIDUES IN SEQ ID NO: (1)..(2717)

<400> SEQUENCE: 21
```

-continued

```
Met Pro Arg Thr Lys Gln Ile His Pro Arg Asn Leu Arg Asp Lys Ile
1               5                   10                  15
Glu Glu Ala Gln Lys Glu Leu Asn Gly Ala Val Ser Lys Lys Glu
            20                  25                  30
Ile Leu Gln Ala Gly Val Lys Gly Thr Ser Glu Ser Leu Lys Gly Val
        35                  40                  45
Lys Arg Lys Lys Ile Val Ala Glu Asn His Leu Lys Lys Ile Pro Lys
50                  55                  60
Ser Pro Leu Arg Asn Pro Leu Gln Ala Lys His Lys Gln Asn Thr Glu
65                  70                  75                  80
Glu Ser Ser Phe Ala Val Leu His Ser Ala Ser Glu Ser His Lys Lys
                85                  90                  95
Gln Asn Tyr Ile Pro Val Lys Asn Gly Lys Gln Phe Thr Lys Gln Asn
            100                 105                 110
Gly Glu Thr Pro Gly Ile Ile Ala Glu Ala Ser Lys Ser Glu Glu Ser
        115                 120                 125
Val Ser Pro Lys Lys Pro Leu Phe Leu Gln Gln Pro Ser Glu Leu Arg
    130                 135                 140
Arg Trp Arg Ser Glu Gly Ala Asp Pro Ala Lys Phe Ser Asp Leu Asp
145                 150                 155                 160
Glu Gln Cys Asp Ser Ser Leu Ser Ser Lys Thr Arg Thr Asp Asn
                165                 170                 175
Ser Glu Cys Ile Ser Ser His Cys Gly Thr Thr Ser Pro Ser Tyr Thr
            180                 185                 190
Asn Thr Ala Phe Asp Val Leu Leu Lys Ala Met Glu Pro Glu Leu Ser
        195                 200                 205
Thr Leu Ser Gln Lys Gly Ser Pro Cys Ala Ile Lys Thr Glu Lys Leu
    210                 215                 220
Arg Pro Asn Lys Thr Ala Arg Ser Pro Lys Leu Lys Asn Ser Ser
225                 230                 235                 240
Met Asp Ala Pro Asn Gln Thr Ser Gln Glu Leu Val Ala Glu Ser Gln
                245                 250                 255
Ser Ser Cys Thr Ser Tyr Thr Val His Met Ser Ala Ala Gln Lys Asn
            260                 265                 270
Glu Gln Gly Ala Met Gln Ser Ala Ser His Leu Tyr His Gln His Glu
        275                 280                 285
His Phe Val Pro Lys Ser Asn Gln His Asn Gln Gln Leu Pro Gly Cys
    290                 295                 300
Ser Gly Phe Thr Gly Ser Leu Thr Asn Leu Gln Asn Gln Glu Asn Ala
305                 310                 315                 320
Lys Leu Glu Gln Val Tyr Asn Ile Ala Val Thr Ser Ser Val Gly Leu
                325                 330                 335
Thr Ser Pro Ser Ser Arg Ser Gln Val Thr Pro Gln Asn Gln Gln Met
            340                 345                 350
Asp Ser Ala Ser Pro Leu Ser Ile Ser Pro Ala Asn Ser Thr Gln Ser
        355                 360                 365
Pro Pro Met Pro Ile Tyr Asn Ser Thr His Val Ala Ser Val Val Asn
    370                 375                 380
Gln Ser Val Glu Gln Met Cys Asn Leu Leu Leu Lys Asp Gln Lys Pro
385                 390                 395                 400
Lys Lys Gln Gly Lys Tyr Ile Cys Glu Tyr Cys Asn Arg Ala Cys Ala
                405                 410                 415
Lys Pro Ser Val Leu Leu Lys His Ile Arg Ser His Thr Gly Glu Arg
            420                 425                 430
```

```
Pro Tyr Pro Cys Val Thr Cys Gly Phe Ser Phe Lys Thr Lys Ser Asn
        435                 440                 445

Leu Tyr Lys His Lys Ser His Ala His Thr Ile Lys Leu Gly Leu
    450                 455                 460

Val Leu Gln Pro Asp Ala Gly Leu Phe Leu Ser His Glu Ser Pro
465                 470                 475                 480

Lys Ala Leu Ser Ile His Ser Asp Val Glu Asp Ser Gly Ser Glu
                485                 490                 495

Glu Glu Gly Ala Thr Asp Glu Arg Gln His Asp Leu Gly Ala Met Glu
            500                 505                 510

Leu Gln Asn Val His Ile Ile Lys Arg Met Ser Asn Ala Glu Thr Leu
    515                 520                 525

Leu Lys Ser Ser Phe Thr Pro Ser Ser Pro Glu Asn Val Ile Gly Asp
530                 535                 540

Phe Leu Leu Gln Asp Arg Ser Ala Glu Ser Gln Ala Val Thr Glu Leu
545                 550                 555                 560

Pro Lys Val Val His His Val Thr Val Ser Pro Leu Arg Thr Asp
                565                 570                 575

Ser Pro Lys Ala Met Asp Pro Lys Pro Glu Leu Ser Ser Ala Gln Lys
        580                 585                 590

Gln Lys Asp Leu Gln Val Thr Asn Val Gln Pro Leu Ser Ala Asn Met
        595                 600                 605

Ser Gln Gly Gly Val Ser Arg Leu Glu Thr Asn Glu Asn Ser His Gln
    610                 615                 620

Lys Gly Asp Met Asn Pro Leu Glu Gly Lys Gln Asp Ser His Val Gly
625                 630                 635                 640

Thr Val His Ala Gln Leu Gln Arg Gln Gln Ala Thr Asp Tyr Ser Gln
                645                 650                 655

Glu Gln Gln Gly Lys Leu Leu Ser Pro Arg Ser Leu Gly Ser Thr Asp
        660                 665                 670

Ser Gly Tyr Phe Ser Arg Ser Glu Ser Ala Asp Gln Thr Val Ser Pro
    675                 680                 685

Pro Thr Pro Phe Ala Arg Arg Phe Pro Ala Gln Asn Lys Thr Leu Glu
690                 695                 700

Gly Val Thr Asp Pro Leu Gln Leu Leu Ser Pro Arg Gln His Pro Leu
705                 710                 715                 720

Leu Cys His Arg Glu Lys Ala Leu Leu Leu Pro Gly Gln Met Arg Pro
                725                 730                 735

Pro Leu Ala Thr Lys Thr Leu Glu Glu Arg Ile Ser Lys Leu Ile Ser
        740                 745                 750

Asp Asn Glu Ala Leu Val Asp Asp Lys Gln Leu Asp Ser Val Lys Pro
        755                 760                 765

Arg Arg Thr Ser Leu Ser Arg Arg Gly Ser Ile Asp Ser Pro Lys Ser
    770                 775                 780

Tyr Ile Phe Lys Asp Ser Phe Gln Phe Asp Leu Lys Pro Val Gly Arg
785                 790                 795                 800

Arg Thr Ser Ser Ser Asp Ile Pro Lys Ser Pro Phe Thr Pro Thr
                805                 810                 815

Glu Lys Ser Lys Gln Val Phe Leu Leu Ser Val Pro Ser Leu Asp Cys
        820                 825                 830

Leu Pro Ile Thr Arg Ser Asn Ser Met Pro Thr Thr Gly Tyr Ser Ala
        835                 840                 845

Val Pro Ala Asn Ile Ile Pro Pro Pro His Pro Leu Arg Gly Ser Gln
```

-continued

```
                850                 855                 860
Ser Phe Asp Asp Lys Ile Gly Ala Phe Tyr Asp Asp Val Phe Val Ser
865                 870                 875                 880

Gly Pro Asn Ala Pro Val Pro Gln Ser Gly His Pro Arg Thr Leu Val
                885                 890                 895

Arg Gln Ala Ala Ile Glu Asp Ser Ser Ala Asn Glu Ser His Val Leu
                900                 905                 910

Gly Thr Gly Gln Ser Leu Asp Glu Ser His Gln Gly Cys His Ala Ala
                915                 920                 925

Gly Glu Ala Met Ser Val Arg Ser Lys Ala Leu Ala Gln Gly Pro His
                930                 935                 940

Ile Glu Lys Lys Lys Ser His Gln Gly Arg Gly Thr Met Phe Glu Cys
945                 950                 955                 960

Glu Thr Cys Arg Asn Arg Tyr Arg Lys Leu Glu Asn Phe Glu Asn His
                965                 970                 975

Lys Lys Phe Tyr Cys Ser Glu Leu His Gly Pro Lys Thr Lys Val Ala
                980                 985                 990

Met Arg Glu Pro Glu His Ser Pro  Val Pro Gly Gly Leu  Gln Pro Gln
                995                 1000                1005

Ile Leu  His Tyr Arg Val Ala  Gly Ser Ser Gly Ile  Trp Glu Gln
        1010                 1015                1020

Thr Pro  Gln Ile Arg Lys Arg  Lys Met Lys Ser  Val Gly Asp
        1025                 1030                1035

Asp Glu  Glu Leu Gln Gln Asn  Glu Ser Gly Thr Ser  Pro Lys Ser
        1040                 1045                1050

Ser Glu  Gly Leu Gln Phe Gln  Asn Ala Leu Gly Cys  Asn Pro Ser
        1055                 1060                1065

Leu Pro  Lys His Ser Val Thr  Ile Arg Ser Asp Gln  Gln His Lys
        1070                 1075                1080

Asn Ile  Gln Leu Gln Asn Ser  His Ile His Leu Val  Ala Arg Gly
        1085                 1090                1095

Pro Glu  Gln Thr Met Asp Pro  Lys Leu Ser Thr Ile  Met Glu Gln
        1100                 1105                1110

Gln Ile  Ser Ser Ala Ala Gln  Asp Lys Ile Glu Leu  Gln Arg His
        1115                 1120                1125

Gly Thr  Gly Ile Ser Val Ile  Gln His Thr Asn Ser  Leu Ser Arg
        1130                 1135                1140

Pro Asn  Ser Phe Asp Lys Pro  Glu Pro Phe Glu Arg  Ala Ser Pro
        1145                 1150                1155

Val Ser  Phe Gln Glu Leu Asn  Arg Thr Gly Asn Ser  Gly Ser Leu
        1160                 1165                1170

Lys Val  Ile Gly Ile Ser Gln  Glu Ser His Pro  Ser Arg Asp
        1175                 1180                1185

Gly Ser  His Pro His Gln Leu  Ala Leu Ser Asp Ala  Leu Arg Gly
        1190                 1195                1200

Glu Leu  Gln Glu Ser Ser Arg  Lys Ser Pro Ser Glu  Arg His Val
        1205                 1210                1215

Leu Gly  Gln Pro Ser Arg Leu  Ile Arg Gln His Asn  Ile Gln Val
        1220                 1225                1230

Pro Glu  Ile Leu Val Thr Glu  Glu Pro Asp Arg Asp  Leu Glu Ala
        1235                 1240                1245

Gln Cys  His Asp Gln Glu Lys  Ser Glu Lys Phe Ser  Trp Pro Gln
        1250                 1255                1260
```

-continued

Arg Ser Glu Thr Leu Ser Lys Leu Pro Thr Glu Lys Leu Pro Pro
   1265              1270                1275

Lys Lys Lys Arg Leu Arg Leu Ala Glu Ile Glu His Ser Ser Thr
   1280              1285                1290

Glu Ser Ser Phe Asp Ser Thr Leu Ser Arg Ser Leu Ser Arg Glu
   1295              1300                1305

Ser Ser Leu Ser His Thr Ser Ser Phe Ser Ala Ser Leu Asp Ile
   1310              1315                1320

Glu Asp Val Ser Lys Thr Glu Ala Ser Pro Lys Ile Asp Phe Leu
   1325              1330                1335

Asn Lys Ala Glu Phe Leu Met Ile Pro Ala Gly Leu Asn Thr Leu
   1340              1345                1350

Asn Val Pro Gly Cys His Arg Glu Met Arg Arg Thr Ala Ser Glu
   1355              1360                1365

Gln Ile Asn Cys Thr Gln Thr Ser Met Glu Val Ser Asp Leu Arg
   1370              1375                1380

Ser Lys Ser Phe Asp Cys Gly Ser Ile Thr Pro Pro Gln Thr Thr
   1385              1390                1395

Pro Leu Thr Glu Leu Gln Pro Pro Ser Ser Pro Ser Arg Val Gly
   1400              1405                1410

Val Thr Gly His Val Pro Leu Leu Glu Arg Arg Arg Gly Pro Leu
   1415              1420                1425

Val Arg Gln Ile Ser Leu Gly Ile Ala Pro Asp Ser His Leu Ser
   1430              1435                1440

Pro Val His Pro Thr Ser Phe Gln Asn Thr Ala Leu Pro Ser Val
   1445              1450                1455

Asn Ala Val Pro Tyr Gln Gly Pro Gln Leu Thr Ser Thr Ser Leu
   1460              1465                1470

Ala Glu Phe Ser Ala Asn Thr Leu His Ser Gln Thr Gln Val Lys
   1475              1480                1485

Asp Leu Gln Ala Glu Thr Ser Asn Ser Ser Ser Thr Asn Val Phe
   1490              1495                1500

Pro Val Gln Gln Leu Cys Asp Ile Asn Leu Leu Asn Gln Ile His
   1505              1510                1515

Ala Pro Pro Ser His Gln Ser Thr Gln Leu Ser Leu Gln Val Ser
   1520              1525                1530

Thr Gln Gly Ser Lys Pro Asp Lys Asn Ser Val Leu Ser Gly Ser
   1535              1540                1545

Ser Lys Ser Glu Asp Cys Phe Ala Pro Lys Tyr Gln Leu His Cys
   1550              1555                1560

Gln Val Phe Thr Ser Gly Pro Ser Cys Ser Ser Asn Pro Val His
   1565              1570                1575

Ser Leu Pro Asn Gln Val Ile Ser Asp Pro Val Gly Thr Asp His
   1580              1585                1590

Cys Val Thr Ser Ala Thr Leu Pro Thr Lys Leu Ile Asp Ser Met
   1595              1600                1605

Ser Asn Ser His Pro Leu Leu Pro Pro Glu Leu Arg Pro Leu Gly
   1610              1615                1620

Ser Gln Val Gln Lys Val Pro Ser Ser Phe Met Leu Pro Ile Arg
   1625              1630                1635

Leu Gln Ser Ser Val Pro Ala Tyr Cys Phe Ala Thr Leu Thr Ser
   1640              1645                1650

Leu Pro Gln Ile Leu Val Thr Gln Asp Leu Pro Asn Gln Pro Ile
   1655              1660                1665

```
Cys Gln Thr Asn His Ser Val Val Pro Ile Ser Glu Glu Gln Asn
    1670                1675                1680

Ser Val Pro Thr Leu Gln Lys Gly His Gln Asn Ala Leu Pro Asn
    1685                1690                1695

Pro Glu Lys Glu Phe Leu Cys Glu Asn Val Phe Ser Glu Met Ser
    1700                1705                1710

Gln Asn Ser Ser Leu Ser Glu Ser Leu Pro Ile Thr Gln Lys Ile
    1715                1720                1725

Ser Val Gly Arg Leu Ser Pro Gln Gln Glu Ser Ser Ala Ser Ser
    1730                1735                1740

Lys Arg Met Leu Ser Pro Ala Asn Ser Leu Asp Ile Ala Met Glu
    1745                1750                1755

Lys His Gln Lys Arg Ala Lys Asp Glu Asn Gly Ala Val Cys Ala
    1760                1765                1770

Thr Asp Val Arg Pro Leu Glu Ala Leu Ser Ser Arg Val Asn Glu
    1775                1780                1785

Ala Ser Lys Gln Lys Lys Pro Ile Leu Val Arg Gln Val Cys Thr
    1790                1795                1800

Thr Glu Pro Leu Asp Gly Val Met Leu Glu Lys Asp Val Phe Ser
    1805                1810                1815

Gln Pro Glu Ile Ser Asn Glu Ala Val Asn Leu Thr Asn Val Leu
    1820                1825                1830

Pro Ala Asp Asn Ser Ser Thr Gly Cys Ser Lys Phe Val Val Ile
    1835                1840                1845

Glu Pro Ile Ser Glu Leu Gln Glu Phe Glu Asn Ile Lys Ser Ser
    1850                1855                1860

Thr Ser Leu Thr Leu Thr Val Arg Ser Ser Pro Ala Pro Ser Glu
    1865                1870                1875

Asn Thr His Leu Ser Pro Leu Lys Cys Thr Asp Asn Asn Gln Glu
    1880                1885                1890

Arg Lys Ser Pro Gly Val Lys Asn Gln Gly Asp Lys Val Asn Ile
    1895                1900                1905

Gln Glu Gln Ser Gln Arg Pro Val Thr Ser Leu Ser Leu Phe Asn
    1910                1915                1920

Ile Lys Asp Thr Gln Gln Leu Ala Phe Pro Ser Leu Lys Thr Thr
    1925                1930                1935

Thr Asn Phe Thr Trp Cys Tyr Leu Leu Arg Gln Lys Ser Leu His
    1940                1945                1950

Leu Pro Gln Lys Asp Gln Lys Thr Ser Ala Tyr Thr Asp Trp Thr
    1955                1960                1965

Val Ser Ala Ser Asn Pro Asn Pro Leu Gly Leu Pro Thr Lys Val
    1970                1975                1980

Ala Leu Ala Leu Leu Asn Ser Lys Gln Asn Thr Gly Lys Ser Leu
    1985                1990                1995

Tyr Cys Gln Ala Ile Thr Thr His Ser Lys Ser Asp Leu Leu Val
    2000                2005                2010

Tyr Ser Ser Lys Trp Lys Ser Ser Leu Ser Lys Arg Ala Leu Gly
    2015                2020                2025

Asn Gln Lys Ser Thr Val Val Glu Phe Ser Asn Lys Asp Ala Ser
    2030                2035                2040

Glu Ile Asn Ser Glu Gln Asp Lys Glu Asn Ser Leu Ile Lys Ser
    2045                2050                2055

Glu Pro Arg Arg Ile Lys Ile Phe Asp Gly Gly Tyr Lys Ser Asn
```

```
                    2060                2065                2070

Glu Glu Tyr Val Tyr Ile Arg Gly Arg Gly Arg Gly Lys Tyr Ile
        2075                2080                2085

Cys Glu Glu Cys Gly Ile Arg Cys Lys Lys Pro Ser Met Leu Lys
        2090                2095                2100

Lys His Ile Arg Thr His Thr Asp Val Arg Pro Tyr His Cys Thr
        2105                2110                2115

Tyr Cys Asn Phe Ser Phe Lys Thr Lys Gly Asn Leu Thr Lys His
        2120                2125                2130

Met Lys Ser Lys Ala His Ser Lys Lys Cys Val Asp Leu Gly Ile
        2135                2140                2145

Ser Val Gly Leu Ile Asp Glu Gln Asp Thr Glu Glu Ser Asp Glu
        2150                2155                2160

Lys Gln Arg Phe Ser Tyr Glu Arg Ser Gly Tyr Asp Leu Glu Glu
        2165                2170                2175

Ser Asp Gly Pro Asp Glu Asp Asp Asn Glu Asn Glu Asp Asp Asp
        2180                2185                2190

Glu Asp Ser Gln Ala Glu Ser Val Leu Ser Ala Thr Pro Ser Val
        2195                2200                2205

Thr Ala Ser Pro Gln His Leu Pro Ser Arg Ser Ser Leu Gln Asp
        2210                2215                2220

Pro Val Ser Thr Asp Glu Asp Val Arg Ile Thr Asp Cys Phe Ser
        2225                2230                2235

Gly Val His Thr Asp Pro Met Asp Val Leu Pro Arg Ala Leu Leu
        2240                2245                2250

Thr Arg Met Thr Val Leu Ser Thr Ala Gln Ser Asp Tyr Asn Arg
        2255                2260                2265

Lys Thr Leu Ser Pro Gly Lys Ala Arg Gln Arg Ala Ala Arg Asp
        2270                2275                2280

Glu Asn Asp Thr Ile Pro Ser Val Asp Thr Ser Arg Ser Pro Cys
        2285                2290                2295

His Gln Met Ser Val Asp Tyr Pro Glu Ser Glu Glu Ile Leu Arg
        2300                2305                2310

Ser Ser Met Ala Gly Lys Ala Val Ala Ile Thr Gln Ser Pro Ser
        2315                2320                2325

Ser Val Arg Leu Pro Pro Ala Ala Ala Glu His Ser Pro Gln Thr
        2330                2335                2340

Ala Ala Gly Met Pro Ser Val Ala Ser Pro His Pro Asp Pro Gln
        2345                2350                2355

Glu Gln Lys Gln Gln Ile Thr Leu Gln Pro Thr Pro Gly Leu Pro
        2360                2365                2370

Ser Pro His Thr His Leu Phe Ser His Leu Pro Leu His Ser Gln
        2375                2380                2385

Gln Gln Ser Arg Thr Pro Tyr Asn Met Val Pro Val Gly Gly Ile
        2390                2395                2400

His Val Val Pro Ala Gly Leu Thr Tyr Ser Thr Phe Val Pro Leu
        2405                2410                2415

Gln Ala Gly Pro Val Gln Leu Thr Ile Pro Ala Val Ser Val Val
        2420                2425                2430

His Arg Thr Leu Gly Thr His Arg Asn Thr Val Thr Glu Val Ser
        2435                2440                2445

Gly Thr Thr Asn Pro Ala Gly Val Ala Glu Leu Ser Ser Val Val
        2450                2455                2460
```

-continued

```
Pro Cys Ile Pro Ile Gly Gln Ile Arg Val Pro Gly Leu Gln Asn
    2465                2470                2475

Leu Ser Thr Pro Gly Leu Gln Ser Leu Pro Ser Leu Ser Met Glu
    2480                2485                2490

Thr Val Asn Ile Val Gly Leu Ala Asn Thr Asn Met Ala Pro Gln
    2495                2500                2505

Val His Pro Pro Gly Leu Ala Leu Asn Ala Val Gly Leu Gln Val
    2510                2515                2520

Leu Thr Ala Asn Pro Ser Ser Gln Ser Ser Pro Ala Pro Gln Ala
    2525                2530                2535

His Ile Pro Gly Leu Gln Ile Leu Asn Ile Ala Leu Pro Thr Leu
    2540                2545                2550

Ile Pro Ser Val Ser Gln Val Ala Val Asp Ala Gln Gly Ala Pro
    2555                2560                2565

Glu Met Pro Ala Ser Gln Ser Lys Ala Cys Glu Thr Gln Pro Lys
    2570                2575                2580

Gln Thr Ser Val Ala Ser Ala Asn Gln Val Ser Arg Thr Glu Ser
    2585                2590                2595

Pro Gln Gly Leu Pro Thr Val Gln Arg Glu Asn Ala Lys Lys Val
    2600                2605                2610

Leu Asn Pro Pro Ala Pro Ala Gly Asp His Ala Arg Leu Asp Gly
    2615                2620                2625

Leu Ser Lys Met Asp Thr Glu Lys Ala Ala Ser Ala Asn His Val
    2630                2635                2640

Lys Pro Lys Pro Glu Leu Thr Ser Ile Gln Gly Gln Pro Ala Ser
    2645                2650                2655

Thr Ser Gln Pro Leu Leu Lys Ala His Ser Glu Val Phe Thr Lys
    2660                2665                2670

Pro Ser Gly Gln Gln Thr Leu Ser Pro Asp Arg Gln Val Pro Arg
    2675                2680                2685

Pro Thr Gly Leu Pro Arg Arg Gln Pro Thr Val His Phe Ser Asp
    2690                2695                2700

Val Ser Ser Asp Asp Asp Glu Asp Arg Leu Val Ile Ala Thr
    2705                2710                2715

<210> SEQ ID NO 22
<211> LENGTH: 876
<212> TYPE: PRT
<213> ORGANISM: Homo sapiens
<300> PUBLICATION INFORMATION:
<308> DATABASE ACCESSION NUMBER: SWISS-PROT/Q9H706
<309> DATABASE ENTRY DATE: 2007-02-06
<313> RELEVANT RESIDUES IN SEQ ID NO: (1)..(876)

<400> SEQUENCE: 22

Met Asp Pro Ala Pro Ser Leu Gly Cys Ser Leu Lys Asp Val Lys Trp
1               5                   10                  15

Ser Ser Val Ala Val Pro Leu Asp Leu Val Ser Thr Tyr Arg Leu
                20                  25                  30

Pro Gln Ile Ala Arg Leu Asp Asn Gly Glu Cys Val Glu Gly Leu Arg
                35                  40                  45

Glu Asn Asp Tyr Leu Leu Ile His Ser Cys Arg Gln Trp Thr Thr Ile
            50                  55                  60

Thr Ala His Ser Leu Glu Glu Gly His Tyr Val Ile Gly Pro Lys Ile
65              70                  75                  80

Glu Ile Pro Val His Tyr Ala Gly Gln Phe Lys Leu Leu Glu Gln Asp
                85                  90                  95
```

-continued

Arg Asp Ile Lys Glu Pro Val Gln Tyr Phe Asn Ser Val Glu Glu Val
        100                 105                 110

Ala Lys Ala Phe Pro Glu Arg Val Tyr Val Met Glu Asp Ile Thr Phe
        115                 120                 125

Asn Val Lys Val Ala Ser Gly Glu Cys Asn Glu Asp Thr Glu Val Tyr
130                 135                 140

Asn Ile Thr Leu Cys Thr Gly Asp Glu Leu Thr Leu Met Gly Gln Ala
145                 150                 155                 160

Glu Ile Leu Tyr Ala Lys Thr Phe Lys Glu Lys Ser Arg Leu Asn Thr
                165                 170                 175

Ile Phe Lys Lys Ile Gly Lys Leu Asn Ser Ile Ser Lys Leu Gly Lys
                180                 185                 190

Gly Lys Met Pro Cys Leu Ile Cys Met Asn His Arg Thr Asn Glu Ser
        195                 200                 205

Ile Ser Leu Pro Phe Gln Cys Lys Gly Arg Phe Ser Thr Arg Ser Pro
        210                 215                 220

Leu Glu Leu Gln Met Gln Glu Gly Glu His Thr Ile Arg Asn Ile Val
225                 230                 235                 240

Glu Lys Thr Arg Leu Pro Val Asn Val Thr Val Pro Ser Pro Pro Pro
                245                 250                 255

Arg Asn Pro Tyr Asp Leu His Phe Ile Arg Glu Gly Arg Tyr Lys
                260                 265                 270

Phe Val Asn Ile Gln Thr Lys Thr Val Val Cys Cys Val Leu Arg
        275                 280                 285

Asn Asn Lys Ile Leu Pro Met His Phe Pro Leu His Leu Thr Val Pro
290                 295                 300

Lys Phe Ser Leu Pro Glu His Leu Val Lys Gly Glu Ser Trp Pro Glu
305                 310                 315                 320

Thr Leu Val His His Trp Leu Gly Ile Cys Gln Glu Gln Phe Asp Ile
                325                 330                 335

Asp Glu Tyr Ser Arg Ala Val Arg Asp Val Lys Thr Asp Trp Asn Glu
                340                 345                 350

Glu Cys Lys Ser Pro Lys Lys Gly Arg Cys Ser Gly His Asn His Val
        355                 360                 365

Pro Asn Ser Leu Ser Tyr Ala Arg Asp Glu Leu Thr Gln Ser Phe His
        370                 375                 380

Arg Leu Ser Val Cys Val Tyr Gly Asn Asn Leu His Gly Asn Ser Glu
385                 390                 395                 400

Val Asn Leu His Gly Cys Arg Asp Leu Gly Gly Asp Trp Ala Pro Phe
                405                 410                 415

Pro His Asp Ile Leu Pro Tyr Gln Asp Ser Gly Asp Ser Gly Ser Asp
                420                 425                 430

Tyr Leu Phe Pro Glu Ala Ser Glu Glu Ser Ala Gly Ile Pro Gly Lys
        435                 440                 445

Ser Glu Leu Pro Tyr Glu Glu Leu Trp Leu Gly Glu Gly Lys Pro Ser
        450                 455                 460

His Gln Pro Leu Thr Arg Ser Leu Ser Glu Lys Asn Arg Cys Asp Gln
465                 470                 475                 480

Phe Arg Gly Ser Val Arg Ser Lys Cys Ala Thr Ser Pro Leu Pro Ile
                485                 490                 495

Pro Gly Thr Leu Gly Ala Ala Val Lys Ser Ser Asp Thr Ala Leu Pro
        500                 505                 510

Pro Pro Pro Val Pro Pro Lys Ser Glu Ala Val Arg Glu Glu Cys Arg

```
                515                 520                 525
Leu Leu Asn Ala Pro Pro Val Pro Pro Arg Ser Ala Lys Pro Leu Ser
            530                 535                 540

Thr Ser Pro Ser Ile Pro Pro Arg Thr Val Lys Pro Ala Arg Gln Gln
545                 550                 555                 560

Thr Arg Ser Pro Ser Pro Thr Leu Ser Tyr Tyr Ser Ser Gly Leu His
                565                 570                 575

Asn Ile Ser Val Thr Lys Thr Asp Thr Asn Pro Ser Glu Ser Thr Pro
                580                 585                 590

Val Ser Cys Tyr Pro Cys Asn Arg Val Lys Thr Asp Ser Val Asp Leu
                595                 600                 605

Lys Ser Pro Phe Gly Ser Pro Ser Ala Glu Ala Val Ser Ser Arg Leu
            610                 615                 620

Ser Trp Pro Asn His Tyr Ser Gly Ala Ser Glu Ser Gln Thr Arg Ser
625                 630                 635                 640

Asp Phe Leu Leu Asp Pro Ser Arg Ser Tyr Ser Tyr Pro Arg Gln Lys
                645                 650                 655

Thr Pro Gly Thr Pro Lys Arg Asn Cys Pro Ala Pro Phe Asp Phe Asp
                660                 665                 670

Gly Cys Glu Leu Leu Ala Ser Pro Thr Ser Pro Val Thr Ala Glu Phe
            675                 680                 685

Ser Ser Ser Val Ser Gly Cys Pro Lys Ser Ala Ser Tyr Ser Leu Glu
            690                 695                 700

Ser Thr Asp Val Lys Ser Leu Ala Ala Gly Val Thr Lys Gln Ser Thr
705                 710                 715                 720

Ser Cys Pro Ala Leu Pro Pro Arg Ala Pro Lys Leu Val Glu Glu Lys
                725                 730                 735

Val Ala Ser Glu Thr Ser Pro Leu Pro Leu Lys Ile Asp Gly Ala Glu
            740                 745                 750

Glu Asp Pro Lys Ser Gly Ser Pro Asp Leu Ser Glu Asp Gln Tyr Phe
            755                 760                 765

Val Lys Lys Gly Met Gln Asp Ile Phe Ser Ala Ser Tyr Pro Phe Ser
770                 775                 780

Ser Pro Leu His Leu Gln Leu Ala Pro Arg Ser Cys Gly Asp Gly Ser
785                 790                 795                 800

Pro Trp Gln Pro Pro Ala Asp Leu Ser Gly Leu Ser Ile Glu Glu Val
                805                 810                 815

Ser Lys Ser Leu Arg Phe Ile Gly Leu Ser Glu Asp Val Ile Ser Phe
            820                 825                 830

Phe Val Thr Glu Lys Ile Asp Gly Asn Leu Leu Val Gln Leu Thr Glu
                835                 840                 845

Glu Ile Leu Ser Glu Asp Phe Lys Leu Ser Lys Leu Gln Val Lys Lys
            850                 855                 860

Ile Met Gln Phe Ile Asn Gly Trp Arg Pro Lys Ile
865                 870                 875

<210> SEQ ID NO 23
<211> LENGTH: 5035
<212> TYPE: DNA
<213> ORGANISM: Homo sapiens

<400> SEQUENCE: 23
cgcgacctca gatcagacgt ggcgacccgc tgaatttaag catattagtc agcggaggaa      60
aagaaactaa ccaggattcc ctcagtaacg gcgagtgaac agggaagagc ccagcgccga     120
```

```
atccccgccc cgcggggcgc gggacatgtg gcgtacggaa gacccgctcc ccggcgccgc    180
tcgtgggggg cccaagtcct tctgatcgag gcccagcccg tggacggtgt gaggccggta    240
gcggccggcg cgcgcccggg tcttcccgga gtcgggttgc ttgggaatgc agcccaaagc    300
gggtggtaaa ctccatctaa ggctaaatac cggcacgaga ccgatagtca acaagtaccg    360
taagggaaag ttgaaaagaa ctttgaagag agagttcaag agggcgtgaa accgttaaga    420
ggtaaacggg tggggtccgc gcagtccgcc cggaggattc aacccggcgg cgggtccggc    480
cgtgtcggcg gcccggcgga tcttttcccgc ccccgttcc tcccgacccc tcacccgcc    540 ctcccttccc ccgccgcccc tcctcctcct ccccggaggg ggcgggctcc ggcgggtgcg    600
ggggtgggcg ggcggggccg ggggtggggt cggcggggga ccgtcccccg accggcgacc    660
ggccgccgcc gggcgcattt ccaccgcggc ggtgcgccgc gaccggctcc gggacggctg    720
ggaaggcccg gcggggaagg tggctcgggg ggcccgtcc gtccgtccgt cctcctcctc    780
ccccgtctcc gcccccggc cccgcgtcct ccctcgggag ggcgcgcggg tcggggcggc    840
ggcggcggcg gcggtggcgg cggcggcggg ggcggcggga ccgaaacccc ccccgagtgt    900
tacagccccc ccggcagcag cactcgccga atcccgggc cgaggagcg agacccgtcg    960 ccgcgctctc ccccctcccg gcgcccaccc ccgcggggaa tccccgcga ggggggtctc    1020 ccccgcgggg gcgcgccggc gtctcctcgt gggggggccg ggccacccct cccacggcgc    1080
gaccgctctc ccaccccctcc tccccgcgcc cccgccccgg cgacggggg ggtgccgcgc    1140 gcgggtcggg gggcggggcg gactgtcccc agtgcgcccc gggcgggtcg cgccgtcggg    1200 cccggggggag gttctctcgg ggccacgcgc gcgtcccccg aagaggggga cggcggagcg    1260
agcgcacggg gtcggcggcg acgtcggcta cccacccgac ccgtcttgaa acacggacca    1320
aggagtctaa cacgtgcgcg agtcggggc tcgcacgaaa gccgccgtgg cgcaatgaag    1380
gtgaaggccg gcgcgctcgc cggccgaggt gggatcccga ggcctctcca gtccgccgag    1440
ggcgcaccac cggcccgtct cgccgccgc gccggggagg tggagcacga gcgcacgtgt    1500
taggacccga aagatggtga actatgcctg ggcagggcga agccagagga aactctggtg    1560
gaggtccgta gcggtcctga cgtgcaaatc ggtcgtccga cctgggtata ggggcgaaag    1620
actaatcgaa ccatctagta gctggttccc tccgaagttt ccctcaggat agctggcgct    1680
ctcgcagacc cgacgcaccc ccgccacgca gttttatccg gtaaagcgaa tgattagagg    1740
tcttggggcc gaaacgatct caacctattc tcaaacttta aatgggtaag aagcccggct    1800
cgctggcgtg gagccgggcg tggaatgcga gtgcctagtg ggccactttt ggtaagcaga    1860
actggcgctg cgggatgaac cgaacgccgg gttaaggcgc ccgatgccga cgctcatcag    1920
accccagaaa aggtgttggt tgatatagac agcaggacgg tggccatgga agtcggaatc    1980
cgctaaggag tgtgtaacaa ctcacctgcc gaatcaacta gccctgaaaa tggatggcgc    2040
tggagcgtcg ggcccatacc cggccgtcgc cggcagtcga gagtggacgg gagcggcggg    2100 gcggcgcgc gcgcgcgcgc gtgtggtgtg cgtcggaggg cggcggcggc ggcggcggcg    2160
ggggtgtggg gtccttcccc cgccccccc cccacgcctc ctcccctcct cccgcccacg    2220
ccccgctccc cgcccccgga gcccgcggga cgctacgccg cgacgagtag gagggccgct    2280
gcggtgagcc ttgaagccta gggcgcgggc ccgggtggag ccgccgcagg tgcagatctt    2340
ggtggtagta gcaaatattc aaacgagaac tttgaaggcc gaagtggaga agggttccat    2400
gtgaacagca gttgaacatg ggtcagtcgg tcctgagaga tgggcgagcg ccgttccgaa    2460
gggacgggcg atggcctccg ttgccctcgg ccgatcgaaa gggagtcggg ttcagatccc    2520
```

```
cgaatccgga gtggcggaga tgggcgccgc gaggcgtcca gtgcggtaac gcgaccgatc  2580
ccggagaagc cggcgggagc cccggggaga gttctctttt ctttgtgaag ggcagggcgc  2640
cctggaatgg gttcgccccg agagaggggc ccgtgccttg gaaagcgtcg cggttccggc  2700
ggcgtccggt gagctctcgc tggcccttga aaatccgggg gagagggtgt aaatctcgcg  2760
ccgggccgta cccatatccg cagcaggtct ccaaggtgaa cagcctctgg catgttggaa  2820
caatgtaggt aagggaagtc ggcaagccgg atccgtaact tcgggataag gattggctct  2880
aagggctggg tcggtcgggc tggggcgcga agcggggctg ggcgcgcgcc gcggctggac  2940
gaggcgcgcg cccccccac gcccggggca cccccctcgc ggccctcccc cgccccaccc  3000
gcgcgcgccg ctcgctccct ccccacccog cgccctctct ctctctctct ccccgctcc  3060
ccgtcctccc ccctcccogg gggagcgccg cgtgggggcg cggcgggggg agaagggtcg  3120
ggacggcagg ggccgcgcgg cggccgccgg ggcggccggc gggggcaggt ccccgcgagg  3180
ggggcccegg ggaccggggg ggccggccgc ggcgcggact ctggacgcga gccgggccct  3240
tcccgtggat cgcccagct gcggcgggcg tcgcggccgc cccegggag cccggcggcg  3300
gcgcggcgcg cccccaccc caccccacg tctcggtcgc gcgcgcgtcc gctggggcg  3360
ggagcggtcg ggcggcggcg gtcggcgggc ggcggggcgg ggcggttcgt cccccgccc  3420
tacccccccg gccccgtccg ccccccgttc ccccctcctc ctcggcgcgc ggcggcggcg  3480
gcggcaggcg gcggaggggc gcggggccgg tcccccccgc cgggtccgcc cccggggccg  3540
cggttccgcg cgcgcctcgc ctcggccggc gcctagcagc cgacttagaa ctggtgcgga  3600
ccaggggaat ccgactgttt aattaaaaca aagcatcgcg aaggcccgcg gcgggtgttg  3660
acgcgatgtg atttctgccc agtgctctga atgtcaaagt gaagaaattc aatgaagcgc  3720
gggtaaacgg cggagtaac tatgactctc ttaaggtagc caaatgcctc gtcatctaat  3780
tagtgacgcg catgaatgga tgaacgagat tcccactgtc cctacctact atccagcgaa  3840
accacagcca agggaacggg cttggcggaa tcagcgggga aagaagaccc tgttgagctt  3900
gactctagtc tggcacggtg aagagacatg agaggtgtag aataagtggg aggccccogg  3960
cgccccccg gtgtccccgc gagggccccg gggcggggtc cgcggccctg cgggccgccg  4020
gtgaaatacc actactctga tcgttttttc actgacccgg tgaggcgggg gggcgagccc  4080
gaggggctct cgcttctggc gccaagcgcc gcccggccg ggcgcgaccc gctccgggga  4140
cagtgccagg tggggagttt gactggggcg gtacacctgt caaacggtaa cgcaggtgtc  4200
ctaaggcgag ctcagggagg acagaaacct cccgtggagc agaagggcaa aagctcgctt  4260
gatcttgatt ttcagtacga atacagaccg tgaaagcggg gcctcacgat ccttctgacc  4320
ttttgggttt taagcaggag gtgtcagaaa agttaccaca gggataactg gcttgtggcg  4380
gccaagcgtt catagcgacg tcgcttttg atccttcgat gtcggctctt cctatcattg  4440
tgaagcagaa ttcgccaagc gttggattgt tcacccacta atagggaacg tgagctgggt  4500
ttagaccgtc gtgagacagg ttagttttac cctactgatg atgtgttgtt gccatggtaa  4560
tcctgctcag tacgagagga accgcaggtt cagacatttg gtgtatgtgc ttggctgagg  4620
agccaatggg gcgaagctac catctgtggg attatgactg aacgcctcta agtcagaatc  4680
ccgcccaggc gaacgatacg gcagcgccgc ggagcctcgg ttggcctcgg atagccggtc  4740
ccccgcctgt ccccgccggc gggccgcccc ccctccacg cgccccgccg cgggagggcg  4800
cgtgccccgc cgcgcgccgg gaccggggtc cggtgcggag tgcccttcgt cctgggaaac  4860
ggggcgcggc cggaaaggcg gccgccccct cgcccgtcac gcaccgcacg ttcgtgggga  4920
```

```
acctggcgct aaaccattcg tagacgacct gcttctgggt cggggtttcg tacgtagcag    4980
agcagctccc tcgctgcgat ctattgaaag tcagccctcg acacaagggt ttgtc         5035
```

METHOD OF ASSESSING COLORECTAL CANCER STATUS IN AN INDIVIDUAL

CROSS REFERENCE TO RELATED APPLICATIONS

This application is a 35 U.S.C. §371 National Phase Entry Application of International Application No. PCT/IE2008/000092 filed Sep. 26, 2008, which designates the U.S., and which claims the benefit of priority under 35 U.S.C. §119(e) of U.S. Provisional Application No. 60/995,915 filed Sep. 28, 2007, the contents of which are incorporated herein by reference in their entirety.

SEQUENCE LISTING

The instant application contains a Sequence Listing which has been submitted in ASCII format via EFS-Web and is hereby incorporated by reference in its entirety. Said ASCII copy, created on Mar. 12, 2010, is named 20100312_SequenceListing_TextFile_048262_067520_US.txt and is 126,441 bytes in size.

TECHNICAL FIELD

The invention relates to a method of assessing colorectal cancer status in an individual which involves the step of assaying a biological sample derived from the individual for the presence of one or more biomarkers associated with the disease. In particular, the invention relates to a method of assisting in clinical decision making during screening of patients symptomatic for colorectal cancer, which involves the step of assaying a serum sample derived from the individual for the presence of one or more biomarkers associated with the disease.

BACKGROUND TO THE INVENTION

Colorectal cancer is the leading cause of cancer related mortality in the western world. Deaths from colorectal cancer can be prevented through effective screening. There is no uniformly agreed specific screening test or panel that helps direct clinical decision making. Recent studies have defined specific antibody responses to tumour related antigens in patients with cancer. Since these antibodies are often triggered by changes in the structure or expression of self proteins in tumour cells, they may serve as potential immunological markers of cancer.

Various technologies have been used to identify cancer-specific antibodies. Phage display offers a powerful platform to identify antibody signatures. However, phage display technology is labour intensive and peptides expressed by phages often do not correspond to native antigens, thus limiting identification of molecular targets in cancer. Several groups have used proteomics approaches to identify tumour antigens. These methods largely rely on tumour cells as a source for potential antigen. Detection of low abundant proteins and membrane proteins is problematic with this approach. The recent advent of large protein arrays provides a unique opportunity to profile antibody signatures from libraries containing thousands of different proteins. A significant advantage of large protein arrays is that complex, antibody repertoires from cohorts of patients can be easily identified.

STATEMENTS OF INVENTION

According to the invention, there is provided a method of determining the colorectal cancer status of an individual, comprising a step of assaying a biological sample obtained from the individual for the presence of a biomarker selected from group comprising: SEQUENCE ID No's 1 to 22, and correlating the presence/absence of the marker(s) with colorectal cancer status. The presence of the biomarker may be detected directly, by assaying for the biomarker protein, or indirectly by assaying for an autoantibody specific to the biomarker, or assaying for a nucleic acid encoding the biomarker. In a preferred embodiment of the invention, the method involves assaying for an autoantibody specific to the or each biomarker. Preferably, the or each biomarker is selected from the group comprising: SEQUENCE ID No's 1 to 12. More preferably, the or each biomarker is selected from the group comprising: SEQUENCE ID No's 1 to 4, 7, 9 and 10.

In one embodiment, the method comprises assaying for at least two biomarkers, at least one selected from, the group comprising: SEQUENCE ID NO's 1 to 18, and at least one selected from the group comprising: SEQUENCE ID NO's 19 to 22. In this way, the method of the invention employs at least one "positive" biomarker (i.e. a biomarker associated with presence of the cancer), and at least one "negative" biomarker (i.e. a biomarker associated with absence of the disease). Ideally, the "positive" biomarker is selected from the group comprising SEQUENCE ID NO's 1 to 12.

In one preferred embodiment, the invention relates to a method of assessing the colorectal cancer status of an individual, comprising:
  contacting an autoantibody-containing biological sample derived from the individual with a protein selected from group comprising SEQUENCE ID No's 1 to 22, under conditions such that an immunospecific protein-autoantibody binding reaction can occur; and
  detecting the presence of an immunospecific protein/autoantigen binding reaction,
wherein the detection of an immunospecific protein/autoantibody binding reaction indicates the colorectal cancer status of the individual.

In one embodiment, the method comprises a step of assaying a biological sample obtained from the individual for the presence of autoantibodies against at least two proteins selected from group comprising SEQUENCE ID NO's 1 to 22. Preferably, the method comprises step of assaying a biological sample obtained from the individual for the presence of autoantibodies against at least three, four, five, six, seven, eight, nine, ten, eleven, twelve, thirteen, fourteen, fifteen, sixteen, seventeen, eighteen, nineteen, twenty, twenty one, twenty two, or twenty three proteins selected from group comprising SEQUENCE ID NO's 1 to 22.

In one embodiment, the method comprises a step of assaying a biological sample obtained from the individual for the presence of autoantibodies against at least one protein selected from group comprising: SEQUENCE ID NO's 1 to 12. In a preferred embodiment, the method comprises a step of assaying a biological sample obtained from the individual for the presence of autoantibodies against at least two proteins selected from group comprising: SEQUENCE ID NO's 1 to 12. In a more preferred embodiment, the method comprises a step of assaying a biological sample obtained from the individual for the presence of autoantibodies against at least three, four, five, six, seven, eight, nine, ten or eleven proteins selected from group comprising: SEQUENCE ID NO's 1 to 12. In a particularly preferred embodiment of the invention, the method comprises a step of assaying a biological, sample obtained from the individual for the presence of autoantibodies against a repertoire of proteins (antigens) comprising, or consisting essentially of, the proteins of SEQUENCE ID NO's 1 to 12. Where a patient is found to be positive for all twelve of these proteins, this correlates with a positive identification of colorectal cancer at 83.7% sensitivity and 80% specificity. Typically, the repertoire of proteins assayed consists of less than 1000 proteins, preferably less than 100 proteins, more preferably less than 50 proteins, and ideally less than 25 proteins.

In a preferred embodiment of the invention, the method comprises a step of assaying a biological sample from the individual for the presence of autoantibodies against one or more of the proteins of SEQUENCE ID No's 1 to 4, 7, 9 and 10, optionally in combination with one, two, three or four proteins selected from the group comprising: SEQUENCE ID NO's 5, 6, 8, 11, and 12. In one particularly preferred embodiment, the method comprises a step of assaying a biological sample obtained from the individual for the presence of autoantibodies against at least three, preferably four, more preferably five, and ideally six, of the proteins of SEQUENCE ID No's 1 to 4, 7, 9 and 10.

The proteins (autoantigens) of SEQUENCE ID No's 1 to 22 may also be employed as biomarkers to assess colorectal cancer disease status in an individual. Thus, in one embodiment, the invention relates to a method of assessing colorectal cancer status in an individual comprising the step of assaying a biological sample derived from the individual for one or more proteins selected from the group comprising: SEQUENCE ID No's 1 to 22, wherein detection of one or more of the proteins indicates the colorectal cancer status of the individual. Typically, the or each protein is selected from the group comprising: SEQUENCE ID NO'S 1 to 12. In one embodiment, the or each protein is selected from the group comprising; SEQUENCE ID NO's 1 to 4, 7, 9 and 10. In the case of serum antigens, detection of the antigen is sufficient to assess colorectal cancer status. In the case of non-circulating tumour antigens, assessment of colorectal cancer status is generally achieved by means of identifying modulated expression (overexpression/aberrant expression) of the antigen when compared with expression of the antigen in a control patient. Generally, this involves immunohistological staining of a tumour biopsy tissue using suitable means such as p53 staining, however many other means of detecting the protein biomarkers of the invention will be apparent to those skilled in the art.

The invention also relates to a kit for assessing colorectal cancer status in an individual, comprising components for detecting and/or measuring the level of an autoantibody against at least one protein selected from the group comprising: SEQUENCE ID No's 1 to 22. In one embodiment, the kit comprises a support having at least one protein selected from group SEQUENCE ID No's 1 to 22 anchored thereon. Preferably, the support comprises at least two proteins anchored thereon. More preferably, the kit comprises a support having three, four, five, six, seven, eight, nine, ten, eleven, twelve, thirteen, fourteen, fifteen, sixteen, seventeen or eighteen proteins anchored thereon. Typically, the kit comprises means for detecting an immunoprecipitation reaction between one or more of the proteins anchored on the support and associated autoantibodies in the patient sample. Suitably, the detection means comprises a labelled anti-IgG antibody. In one embodiment, the support is selected from the group comprising: a microtitre plate; a glass slide; a polymer membrane; and an affinity column. In one particularly preferred embodiment of the invention, the kit comprises an ELISA™ kit adapted to detect autoantibodies against one or more of the proteins of SEQUENCE ID No's 1 to 22. In another embodiment, the kit comprises a protein array comprising one or more of the proteins of SEQUENCE ID No's 1 to 22. In another embodiment of the invention, autoantibodies may be detected by means of a Western Blot. Typically, the array consists of less than 1000 proteins, preferably less than 500 proteins, preferably less than 200 proteins, preferably less than 100 proteins, and preferably less than 50 proteins, anchored thereon. In a particularly preferred embodiment, the array comprises the proteins of SEQUENCE ID No's 1 to 4, 7, 9 and 10. Typically, the array will also include one or more positive controls, i.e. a protein specific to an antibody present in a normal human serum sample, and one or more negative controls, i.e. a protein specific to an antibody not normally present in a human serum sample, such as an antibody specific to a prokaryotic protein. In another embodiment of the invention, autoantibodies may be detected by means of a Western Blot.

As indicated above, the methods, assays and kits of the invention employ biomarkers (proteins or antibodies specific to the proteins) as a means of assessing colorectal cancer status in an individual. In one preferred embodiment of the invention, the methods, assays, and kits may be employed as a clinical screening tool to assist in the identification of individuals, especially symptomatic individuals, who should be subjected to more invasive investigations, such as colonoscopy. In this regard, it should be noted that many patients who present with symptoms of colorectal cancer (i.e. rectal bleeding, weight loss) often turn out to be negative for colorectal cancer, yet still have to undergo colonoscopy to reach that diagnosis. In this regard, the present invention provides a useful clinical decision making tool which can assist a clinician in identifying those symptomatic patients that are most at risk of having the cancer, thereby potentially reducing the numbers of patients who have to undergo colonoscopy needlessly.

Referring to FIG. 3 below, there is provided a list of biomarkers (SEQUENCE ID NO's 1 to 12) along with data showing the presence of these biomarkers (or rather the presence of autoantibodies specific to these biomarkers) in each patient of the two cohorts of symptomatic patients (cancer v non-cancer controls). It will be evident that the skilled person, using the data in FIG. 3, will be able to choose a repertoire of biomarkers that provides a desired risk assessment of colorectal cancer. Thus, if the chosen repertoire comprises all twelve biomarkers, such a repertoire would be capable of identifying colorectal cancer in an individual with 80% specificity and 83.7% sensitivity. In other words, only 7 of the 43 colorectal cancer patients were negative for all of the 12 biomarkers; 36 of the 43 were positive for at least one of the biomarkers. Thus, if antibodies to all 12 proteins are identified in serum from a patient, this indicates that there is a strong likelihood that they are colorectal cancer positive, and would also provide a very strong indication that they should undergo a colonoscopy. Likewise, if antibodies to a repertoire of 6 biomarkers (for example, ZN700, CADM1, p53, ICLN, LASS5, and TFE2) are identified, FIG. 3 indicates that half of the colorectal cancer patients were positive for antibodies to at least one of these proteins. Thus, again, this would provide an indication to a clinician that the patient should have a colonoscopy. Given the data present in FIG. 3 (optionally in combination with the data in Table II), it is possible for the skilled person to choose a specific repertoire of biomarkers to correlate with a desired % risk of the patient having colorectal cancer.

Thus, in one embodiment, the invention relates to a method of determining colorectal cancer status in an individual, the method comprising a step of assaying a biological sample from the individual for a combination of a plurality of biomarkers selected from SEQUENCE ID NO's: 1 to 12, the combination of biomarkers being chosen such that detection of all biomarkers in the patient correlates to at least a 50% risk of the patient being positive for colorectal cancer. Typically, the combination of biomarkers is chosen such that detection of all biomarkers in the patient correlates to at least a 60% risk of the patient being positive for colorectal cancer. Suitably, the combination of biomarkers is chosen such that detection of all biomarkers in the patient correlates to at least a 70% risk of the patient being positive for colorectal cancer. Ideally, the combination of biomarkers is chosen such that detection of all biomarkers in the patient correlates to at least a 80% risk of the patient being positive for colorectal cancer.

Typically, the combination will comprise at least four biomarkers, preferably at least five biomarkers, more preferably at least six biomarkers, and ideally at least seven biomarkers.

The invention also relates to a method of identifying advanced colorectal cancer in an individual, comprising the step of assaying a biological fluid sample from the individual for antibodies to p53, wherein the presence of p53 antibodies in the biological fluid sample is indicative of advanced colorectal cancer. In this specification, the term "advanced colorectal cancer" should be understood to mean Dukes stage C or D. Typically, the biological fluid is blood, or a blood derivative such as serum.

The invention also relates to a method of diagnosing, or assisting in the diagnosis of, colorectal cancer in an individual, comprising the step of assaying a tumour sample (tissue or cells) for cytoplasmic expression of HMGB1, wherein the presence of HMGB1 in the cytoplasm of tumour cells is indicative of the tumour cells being malignant.

In this specification, the term "biological sample" may be any sample obtained from an individual such as, for example, blood, serum, saliva, urine, cerebrospinal fluid, tissue, cells, etc. Suitably, when the biomarker being assayed is an autoantibody, the biological sample will be serum. In many cases, the individual will be a person suspected of having colorectal cancer, or pre-disposed to developing colorectal cancer as determined by other phenotypic, genotypic or hereditary traits. In other cases, the individual may be a person known to have colorectal cancer, and who is underingoing a therapeutic treatment regime, in which case the method of the invention may be employed to monitor the effectiveness of the treatment, or may be a post-operative patient being monitored for re-occurance of the disease.

In this specification, the term "colorectal cancer status" when used with reference to an individual primarily refers to the risk of the individual having the cancer. Depending on the number of biomarkers detected in the individual, the assay and methods of the invention will assist a clinician is determining the risk that the individual is positive for colorectal cancer. Thus, in one embodiment, the methods, assays and kits of the invention provide a means for screening patients that are symptomatic of colorectal cancer to identify those patients that should undergo further investigative procedures, such as colonoscopy. However, the term also encompasses prognostic evaluation of the cancer, identification of predisposition to developing the cancer, staging of the cancer, and evaluation or monitoring of the progress of the cancer, in the individual. The latter evaluation is typically employed as a means of monitoring the effectiveness of a treatment for the cancer.

Typically, the proteins (autoantigens) selected from the group comprising SEQUENCE ID No's 1 to 22 that are employed to assay for autoantibodies in the individual will comprise the full sequence proteins as provided in the Sequence Listing below, or variants thereof that retain the ability to form an immunogenic complex with the complementary autoantibody. However, it will be understood that antigenic peptides derived from these proteins may also be employed to assay for the autoantibodies, provided that the peptides retain the ability to form an immunospecific autoantibody/autoantigen binding reaction with the relevant antibody. In this context, the term "autoantigen" as used in this specification should be taken to mean one or more of the proteins of SEQUENCE ID No's 1 to 22, or antigenic variants thereof, and antigenic peptides derived therefrom which possess the necessary epitope(s) to form an immunospecific complex with the relevant autoantibody. Methods of deriving antigenic peptides from native antigenic proteins will be well known to those skilled in the art.

An "antigenic variant" of one of the proteins of SEQUENCE ID No's 1 to 22 shall be taken to mean proteins having amino acid sequences which are substantially identical to wild-type protein and which retain the ability to form an immunospecific complex with an autoantibody against the wild-type protein. Thus, for example, the term should be taken to include proteins or polypeptides that are altered in respect of one or more amino acid residues. Preferably such alterations involve the insertion, addition, deletion and/or substitution of 5 or fewer amino acids, more preferably of 4 or fewer, even more preferably of 3 or fewer, most preferably of 1 or 2 amino acids only. Insertion, addition and substitution with natural and modified amino acids is envisaged. The variant may have conservative amino acid changes, wherein the amino acid being introduced is similar structurally, chemically, or functionally to that being substituted. Typically, proteins which have been altered by substitution or deletion of residues located at an immunologically important part of the given protein, such as an epitope region, will be excluded from the term "variant". Generally, the variant will have at least 70% amino acid sequence homology, preferably at least 80% sequence homology, more preferably at least 90% sequence homology, and ideally at least 95%, 96%, 97%, 98% or 99% sequence homology with the wild-type protein. In this context, sequence homology comprises both sequence identity and similarity, i.e. a polypeptide sequence that shares 70% amino acid homology with a wild-type human protein is one in which any 70% of aligned residues are either identical to, or conservative substitutions of, the corresponding residues in the wild-type human protein.

The term "variant" is also intended to include chemical derivatives of the wild-type protein, i.e. where one or more residues is chemically derivatized by reaction of a functional side group. Also included within the term variant are protein molecules in which naturally occurring amino acid residues are replaced with amino acid analogues.

Proteins and polypeptides (including variants and fragments thereof) for use in the invention may be generated wholly or partly by chemical synthesis or by expression from nucleic acid. The proteins and peptides for use in the present invention can be readily prepared according to well-established, standard liquid or, preferably, solid-phase peptide synthesis methods known in the art [2]. As an alternative, the proteins for use in the invention (and as described in the attached Sequence Listing) may be obtained from commercially available recombinant bacterial clones that are genetically engineered to inducibly express the protein of interest. Bacterial clones capable of expressing the proteins of the sequence Listing may be obtained from RZPD in Germany. As an alternative, prokaryotic and eukaryotic expression systems suitable for generating the proteins of the Sequence Listing are commercially available, and the use of these systems to generate the desired proteins would be a routine task for the person skilled in the field of molecular biology. In this regard, it is intended that the peptides and proteins for use in the invention would also include those having post translation modification such as phosphorylation and glycosylation, as a result of the protein being generated in a eukaryotic expression system, or indeed in a human. Moreover, commercial sources of these proteins are available, and are referenced in a number of publicly available protein databases, including NCBI, SWISSPROT and TREMBLE.

Methods for assaying a biological sample for the presence of one or more autoantibodies will be well known to those skilled in the art. Such methods include immunoassays that include, but are not limited to, immunoprecipitation assays, ELISA-based assays [1], radioimmunoassay, "sandwich" immunoassays, immunodiffusion assays, agglutination assays, and western blot assays. In one example, the selected autoantigen is immobilised on a glass slide in such a manner that the autoantigen is available to form an immunological complex with any specific autoantibodies present in the serum sample reacted with the slide. The glass slide is then brought into contact with the serum sample from an individual, and the autoantigens on the slide are allowed to react with the serum for a suitable period of time. The slide is then washed to remove non-reacting protein, and the antibodies that remain on the slide and that have reacted with the autoantigens on the slide are detected using conventional techniques (i.e. by reacting with a radioactive anti-IgG antibody). Methods of immobilising proteins on a glass slide, and methods of identifying bound IgG antibodies will be well known to those skilled in the art.

Other methods of detecting biomarkers will be well known to those skilled in the field of proteomics. For example, protein arrays may be generated that are custom-made to assay for the presence of specific auto-antibodies. The company RZPD provide a service for the production of customised macro-arrays. Other methods for the detection of the biomarkers of the invention would be the use of ELISA's, the details of which will be well known to those skilled in the field.

The proteins used in these techniques can be prepared using standard recombinant DNA techniques along with the sequence information provided herein and in the cross-referenced NCBI database (see Sequence Listing). In the case of many of the proteins of SEQUENCE ID NO's 1 to 22, bacterial clones engineered to express the protein of interest are available from various commercial sources.

Where the method of the invention involves determining the presence in the biological sample of autoantigens, various methods of making such a determination will be apparent to the person skilled in the art. For examples, antibodies against the autoantigen of interest may be raised using conventional techniques, and may be employed as diagnostic reagents in an autoantigen assay. An antibody against a protein of the Sequence Listing may be a monoclonal or polyclonal antibody or other specific binding partner, as long as it can recognize the protein. Antibodies can be produced by using a protein selected from the group of Sequence ID No's 1 to 22 as the antigen according to a conventional antibody or antiserum preparation process. The present invention contemplates the use of both monoclonal and polyclonal antibodies in methods of detecting the presence of circulating or tumor antigens. Any suitable method may be used to generate the antibodies used in the methods and kits of the present invention, including but not limited to, those disclosed herein. For example, for preparation of a monoclonal antibody, protein, as such, or together with a suitable carrier or diluent is administered to an animal under conditions that permit the production of antibodies. For enhancing the antibody production capability, complete or incomplete Freund's adjuvant may be administered. Normally, the protein is administered once every 2 weeks to 6 weeks, in total, from about 2 times to about 10 times. Animals suitable for use in such methods include, but are not limited to, primates, rabbits, dogs, guinea pigs, mice, rats, sheep, goats, etc.

For preparing monoclonal antibody-producing cells, an individual animal whose antibody titer has been confirmed (e.g., a mouse) is selected, and 2 days to 5 days after the final immunization, its spleen or lymph node is harvested and antibody-producing cells contained therein are fused with myeloma cells to prepare the desired monoclonal antibody producer hybridoma. Measurement of the antibody titer in antiserum can be carried out, for example, by reacting the labeled protein, as described hereinafter and antiserum and then measuring the activity of the labeling agent bound to the antibody. The cell fusion can be carried out according to known methods [3]. As a fusion promoter, for example, polyethylene glycol (PEG) or Sendai virus (HVJ), preferably PEG is used.

Polyclonal antibodies may be prepared by any known method or modifications of these methods including obtaining antibodies from patients. For example, a complex of an immunogen (an antigen against the protein) and a carrier protein is prepared and an animal is immunized by the complex according to the same manner as that described with respect to the above monoclonal antibody preparation. A material containing the antibody is recovered from the immunized animal and the antibody is separated and purified. As to the complex of the immunogen and the carrier protein to be used for immunization of an animal, any carrier protein and any mixing proportion of the carrier and a hapten can be employed as long as an antibody against the hapten, which is crosslinked on the carrier and used for immunization, is produced efficiently.

The antibodies may be labelled with a detectable label such as, for example, a fluorescent, luminescent, or radioactive label. Typically, the antibodies will be immobilised to a support, before the support is reacted with a biological sample. The support will then be washed to remove any non-reacting proteins, before any proteins that have formed an immunospecific complex with the antibodies are identified using conventional techniques. Generally, this method is suitable for detecting the presence of autoantigens in biological fluid samples. When the autoantigen is a tumor antigen, in other words, when it is expressed by a tumor cell, the most appropriate method of detection is immunohistochemical detection. Methods of immunohistochemical detection of tumor antigens will be well known to those skilled in the art, and are described previously.

In cases where the method of the invention involves detecting the presence of autoantigens (whether the autoantigen is a circulating, tumor, or other type, of antigen), detection may be carried by measuring the expression of corresponding mRNA from a tumour-derived tissue or cell sample. mRNA expression may be measured by any suitable method including, but not limited to, a Northern Blot or detection by hybridisation to a oligonucleotide probe. A variety of hybridization assays using a variety of technologies for hybridization and detection are available. For example, a TaqMan assay (PE Biosystems, Foster City, Calif.; See e.g., U.S. Pat. Nos. 5,962,233 and 5,538,848) is utilized. The assay is performed during a PCR reaction. The TaqMan assay exploits the 5'-3' exonuclease activity of the AMPLITAQ GOLD DNA polymerase. A probe consisting of an oligonucleotide with a 5'-reporter dye (e.g., a fluorescent dye) and a 3'-quencher dye is included in the PCR reaction. During PCR, if the probe is bound to its target, the 5'-3' nucleolytic activity of the AMPLITAQ GOLD polymerase cleaves the probe between the reporter and the quencher dye. The separation of the reporter dye from the quencher dye results in an increase of fluorescence. The signal accumulates with each cycle of PCR and can be monitored with a fluorometer.

In other embodiments, reverse-transcriptase PCR (RT-PCR) is used to detect the expression of RNA where RNA is enzymatically converted to complementary DNA or "cDNA" using a reverse transcriptase enzyme. The cDNA is then used as a template for a PCR reaction. PCR products can be detected by any suitable method, including but not limited to, gel electrophoresis and staining with a DNA specific stain or hybridization to a labeled probe. In some embodiments, the quantitative reverse transcriptase PCR with standardized mixtures of competitive templates method described in U.S. Pat. Nos. 5,639,606, 5,643,765, and 5,876,978 is utilized.

In cases where the biomarker being assayed is the autoantigen, in-vivo imaging techniques may be employed to detect the presence of the markers. For example, one or more of the proteins of Sequence ID No's 1 to 22, or mRNA encoding one or more of these protein, is labeled using an labeled antibody specific for the protein. A specifically bound and labeled antibody can be detected in an individual using an in vivo imaging method, including, but not limited to, radionuclide imaging, positron emission tomography, computerized axial tomography, X-ray or magnetic resonance imaging method, fluorescence detection, and chemiluminescent detection. Methods for generating antibodies to the proteins of the Sequence Listing are described above. In some embodiments, reagents (e.g., antibodies) specific for a specific biomarker are fluorescently labeled. The labeled antibodies are introduced into a subject (e.g., orally or parenterally). Fluorescently labeled antibodies are detected using any suitable method (e.g., using the apparatus described in U.S. Pat. No. 6,198,107). In other embodiments, antibodies are radioactively labeled. The use of antibodies for in-vivo diagnosis is well known in the art. Sumerdon et al [4] have described an optimized antibody-chelator for the radioimmunoscintographic imaging of tumors using Indium-111 as the label. Griffin et al, [5] have described the use of this agent in detecting tumors in patients suspected of having recurrent colorectal cancer. The use of similar agents with paramagnetic ions as labels for magnetic resonance imaging is known in the art [6]. The label used will depend on the imaging modality chosen. Radioactive labels such as Iridium-111, Technetium-99m, or Iodine-131 can be used for planar scans or single photon emission Computed tomography (SPECT). Positron emitting labels such as Fluorine-19 can also be used for positron emission tomography (PET). For MRI, paramagnetic ions such as Gadolinium (EI) or Manganese (II) can be used.

A) A representative section of the hEx1 protein array screened with serum from a colorectal cancer patient (left panel) and a non-cancer control (right panel). The left panel demonstrates two positive signals (duplicate clones) for the p53 antibody in serum of a colorectal cancer patient (p53+), which is absent in the right control panel (p53−).

B) Immunohistochemical staining of colorectal cancer and normal colorectal tissue using monoclonal antibody to p53 (DO-7). Original magnification: ×40. Left panel demonstrates colorectal cancer tissue with strong nuclear p53 staining; right panel demonstrates cancer free colorectal tissue with weak nuclear p53 staining.

C) The intensity of p53 staining in tumour tissue increases with advanced Dukes' stage as identified by immunohistochemical analysis of all 43 examined cases.

Figure 5A:
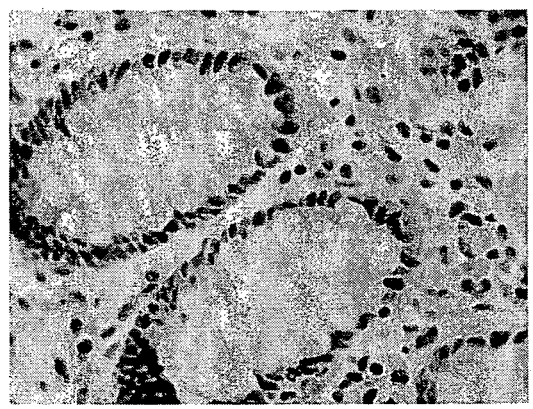
Figure 5B:
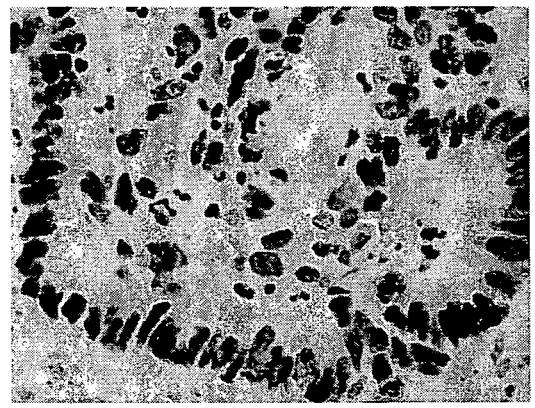
Figure 5C:
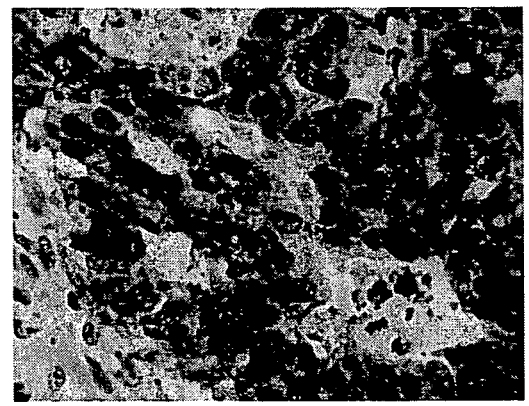

FIG. 5: HMGB1 expression in tissue.

Immunohistochemical staining of colorectal cancer and normal colorectal tissue using monoclonal antibody to HMGB1 (M02, 1D5). Original magnification: ×40

A: Normal colorectal tissue showing nuclear staining for HMGB1 with no cytoplasmic staining.

B: Colorectal cancer tissue showing nuclear staining for HMGB1 with no cytoplasmic staining C: Colorectal cancer tissue showing nuclear and strong cytoplasmic staining for HMGB1.

DETAILED DESCRIPTION OF THE INVENTION

Patient Samples 1,820 patients attending the colonoscopy clinic were screened until a training set of 20 colorectal cancer and 20 sex- and age-matched patients with no cancer was identified. In total, 43 colorectal cancer patients and 40 non-cancer patients entered the study. All 83 sera were screened on high density protein arrays and individual profiles were characterised. To identify a colorectal cancer-specific antibody signature, the frequencies of antibodies in a sex- and age-matched training set were analysed. The resulting antibody profiles identified in the training set were further characterised in an additional extended cohort. The expression of identified antigens p53 and HMGB1 in tissue from this cohort of patients was characterised to validate the approach and assess their potential as molecular marker of cancer.

Antibody Profiles

Figure 1:
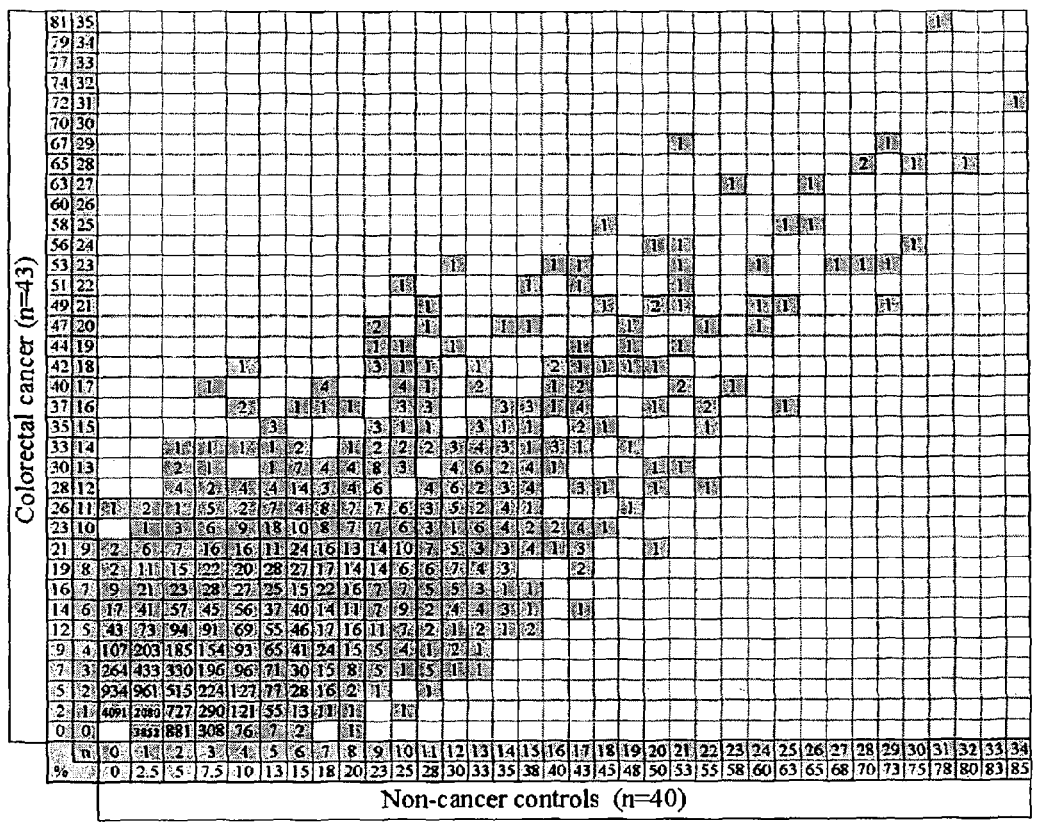
FIG. 1: The frequency distribution of antibodies among colorectal cancer patients and non-cancer controls is heterogeneous. The X-axis shows the cumulative number of non-cancer patients. Percentage is shown below. The Y-axis shows the cumulative number of colorectal cancer patients. Percentage is shown aside. The numbers in the grid are the numbers of clones identified. Thus, multiple antibodies are identified in individual subjects.

The antibody profiles for all 83 subjects were characterised in the absence of any clinical information. The antibody profile for each subject was characterised and resulted in the identification of an average of 833 positives for each patient. Although individual profiles were unique, many of the positives were found to be shared by different individuals. Combining all 83 profiles revealed that 19,645 different clones were positive in one or more patients. This corresponds to 52% of all clones present on the hEx1 protein array. 11,703 clones were positive in two or more sera. When this analysis was done, the clinical information was unblinded and the data analysed as patients with and without cancer (FIG. 1). The diagram illustrates a heterogeneous distribution of antibodies among colorectal cancer patients and non-cancer controls. Antibodies to more than 5,000 antigens were identified exclusively in each group. The remaining antigens were shared between cancer and non-cancer patients.

Analysis of the Antibody Repertoire

Figure 2:
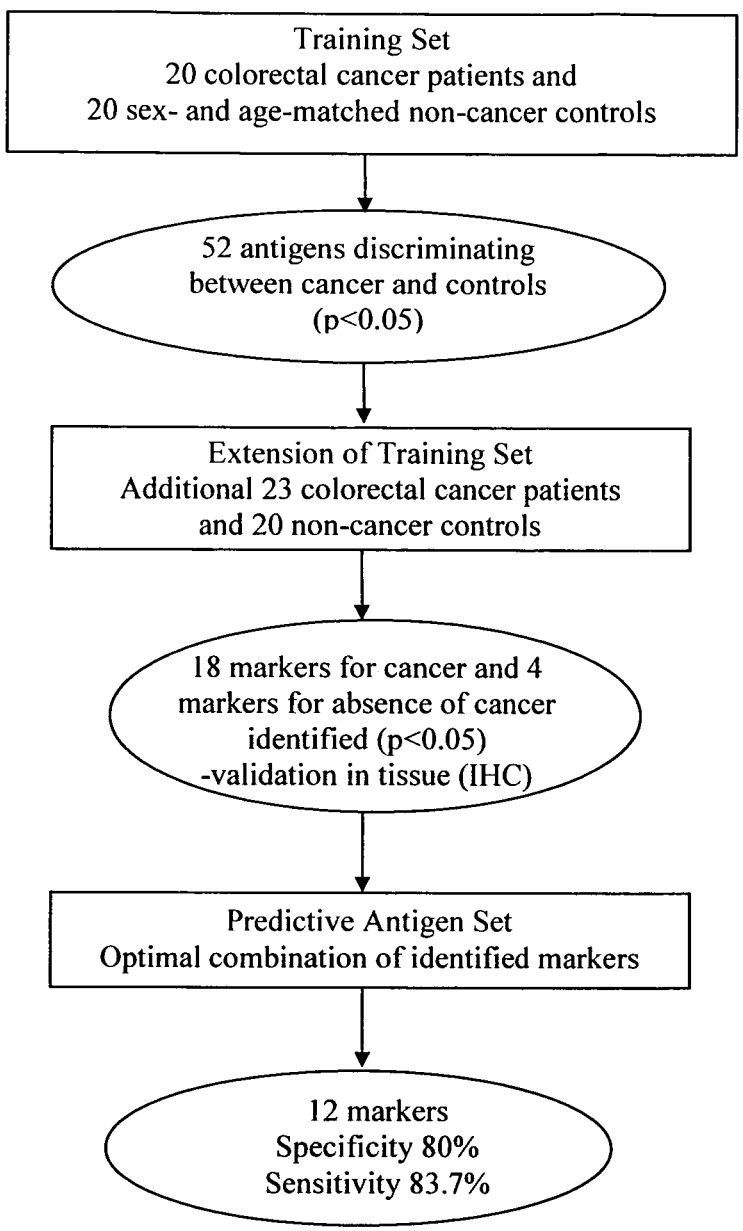
FIG. 2: Strategy to analyse experimental data.
The flowchart delineates sample usage and designation, to training and validation sets, as well as the statistical results of sequential evaluation.

The analysis strategy of the serum screening data is shown in FIG. 2. Twenty cancer patients and 20 non-cancer control patients were sex- and age-matched (Table 1).

TABLE 1

|  | Colorectal cancer Patients (n = 20) | Non-cancer controls (n = 20) |
|---|---|---|
| Sex, n (%) | | |
| Female | 10 (50%) | 10 (50%) |
| Male | 10 (50%) | 10 (50%) |
| Age at diagnosis, years | | |
| Median (interquartile range [IQR]) | 62 (51-67) | 61 (50-69) |
| Smoking | | |
| never | 16 | 15 |
| current | 2 | 3 |
| Ex-smoker | 2 | 2 |
| Alcohol | | |
| none | 6 | 4 |
| less than 10 units per week | 7 | 14 |
| 10-20 units per week | 3 | 0 |
| 21-30 units per week | 2 | 1 |
| more than 30 units per week | 2 | 0 |
| Aspirin | | |
| no | 16 | 14 |
| yes | 4 | 6 |

This group was used as a training set to identify cancer and non-cancer associated antibody profiles. All positives identified on the array were ranked according to statistical significance to discriminate between cancer and control patients. All positives with p values less than 0.05 were considered significant. Antibodies to 43 antigens in the cancer group and 9 antigens in the non-cancer control group correlated significantly with presence or absence of colorectal cancer. The sample size was expanded to characterise the total cohort identified during the study. Of the antigens identified in the training set, 18 antigens from the cancer group and 4 from the non-cancer group were confirmed in the extended set. These verified antigens, significantly discriminating between patients with and without cancer ($p<0.05$), are listed in Table 2 below (Sequence ID NO's 1 to 22). The nucleotide sequence of the gene coding for 28S Ribosomal RNA protein (Sequence ID No: 20) is provided in Sequence ID No: 23.

TABLE 2

| Clone File: | SeqID No: | BLAST Output Description: | Swiss-Prot ID | Cancer (n = 43): Controls (n = 40) |
|---|---|---|---|---|
| O10579 | 1 | Zinc finger protein 700 | ZN700 | 9:0 |
| L03527 | 2 | Tumour suppressor in lung cancer 1 | CADM1 | 9:0 |
| M17513 | 3 | Longevity assurance homolog 5 | LASS 5 | 8:0 |
| G19547 | 4 | Cellular tumor antigen P53 | P53 | 8:0 |
| D15597 | 5 | Zinc finger protein 768 | Q96CX4 | 14:3 |
| I12603 | 6 | Zinc finger protein 638 | ZN638 | 13:3 |
| G07590 | 7 | Methylosome subunit pICln | ICLN | 7:0 |
| P11513 | 8 | Zinc finger protein 346 | ZN346 | 11:2 |
| B13599 | 9 | Transcription factor E2 alpha | TFE2 | 6:0 |
| N17517 | 10 | KIAA0310 protein | AOPJ75 | 6:0 |
| B12538 | 11 | High mobility group protein B1 | HMGB1 | 8:1 |
| L03561 | 12 | Unnamed protein product | BAC85857 | 11:3 |
| I23580 | 13 | Protein ITFG3 | ITFG3' | 17:3 |
| M02600 | 14 | Synaptosomal-associated protein 29 | SNP29 | 12:2 |
| N24509 | 15 | Erythrocyte band 7 integral membrane protein | STOM | 14:4 |
| O11570 | 16 | Transcription cofactor vestigial like protein 4 | VGLL4 | 10:2 |
| C11583 | 17 | Transcription intermediary factor 1-beta | TIF1B | 8:2 |
| F16591 | 18 | Heterogenous nuclear ribonucleoprotein D-like | HNRDL | 17:7 |
| M12552 | 19 | Hypothetical protein FLJ10154 | FLJ10154 | 3:13 |
| E17585 | 20 | 28S ribosomal RNA | NR_003287 | 4:12 |
| C23550 | 21 | Positive regulatory domain II-binding factor | ZEP1 | 1:7 |
| E09582 | 22 | Protein FAM59A | FA59A | 8:17 |

Figure 3:
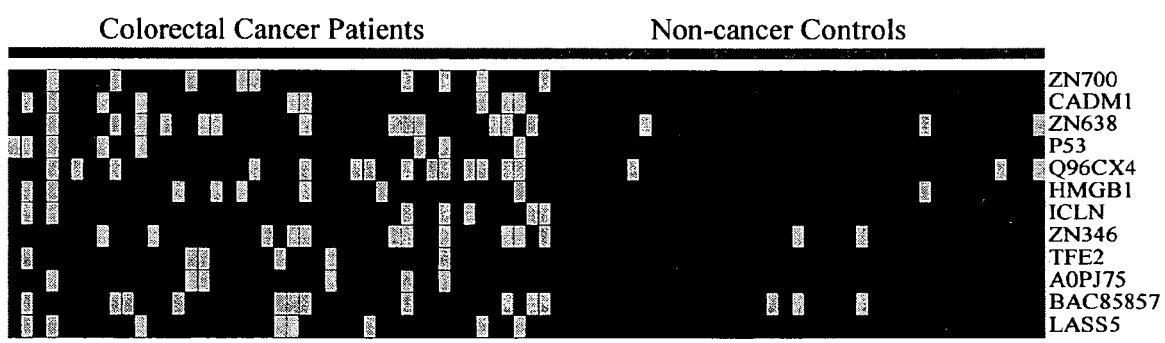
FIG. 3: Antibody signature for colorectal cancer. Distribution map of 12 predictive markers between patients. The rows represent the antigens and the columns represent colorectal cancer patients and non-cancer control patients. Antigens reactive with sera are presented with a lighter grey box. The 12 antigens identify cancer with 80% specificity and 83.7% sensitivity in 43 cancer patients and 40 non-cancer controls.

An optimal antigen combination to discriminate between patients with and without colorectal cancer was determined. All antigens identified in the extended set were examined separately. Starting with the antigen most significantly associated with cancer versus the non-cancer group, a predictive ability was calculated based on specificity and sensitivity. By stepwise adding next ranked antigens, the predictive ability of the combined antigens was reassessed until the optimal combination was found. The analysis resulted in a subset of 12 antigens discriminating between, colorectal cancer patients and 40 non-cancer control patients with 80% specificity and 83.7% sensitivity (FIG. 3).

Identified Cancer Antigens

Analysis of the array data in the training set and the extended set identified 18 antigens in the cancer group and antigens associated with absence of cancer (Table 2). These antigens range from membrane proteins (CADM1), cytoplasmic proteins (SNP29), nuclear proteins (p53, HMGB1) and hypothetical proteins.

Figure 4A:
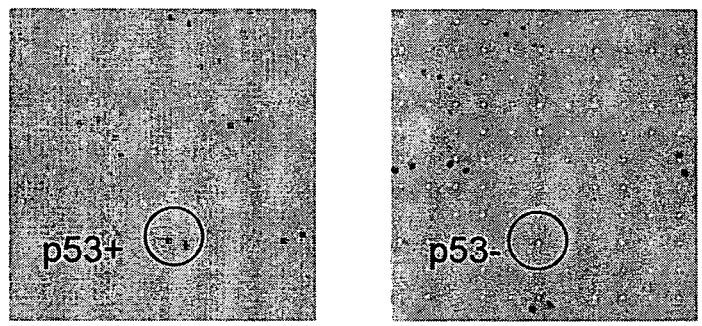
FIG. 4: p53 antibodies correlate with expression in cancer tissue.
Figure 4B:
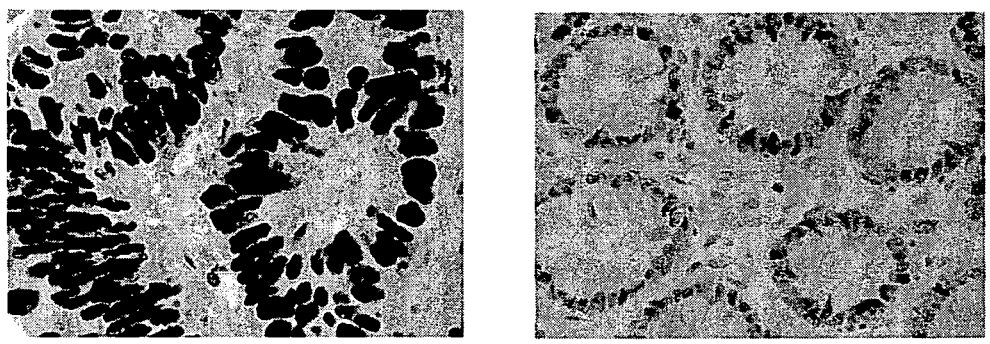
Figure 4C:
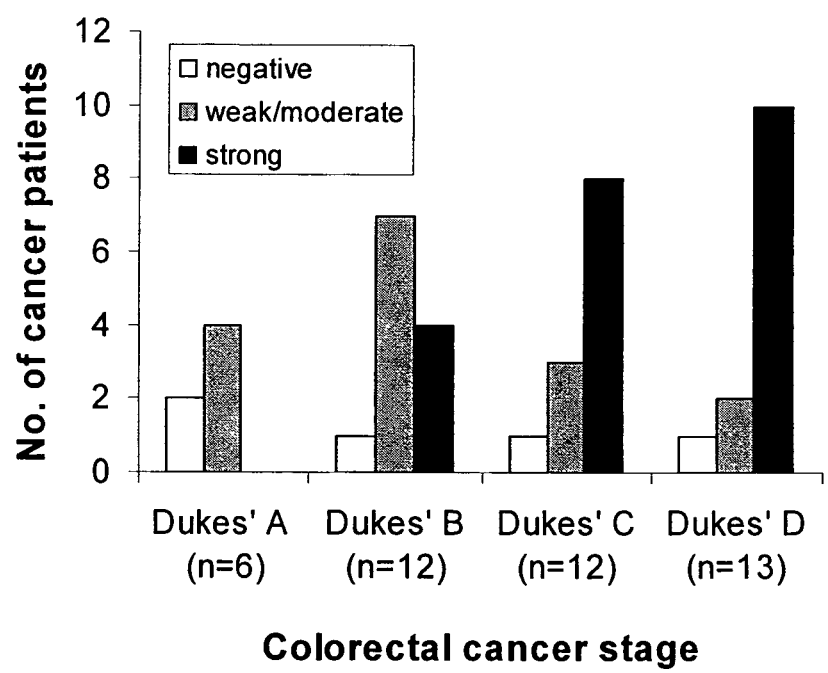

Antibodies to p53 were identified in 19% of patients with colorectal cancer and were absent in non-cancer, controls. Representative sections of the hEx1 protein array showing positive and negative p53 signals are shown in FIG. 4A. Since several studies have demonstrated that accumulation of mutant p53 protein in tumour cells results in p53 antibodies in the sera of colorectal cancer patients, p53 protein expression was characterised in the patient cohort to validate the approach. Tissue samples from excised cancers were examined. Tissue microarrays were constructed from the same group of patients used in the serum screening. Immunohistochemistry results showed that p53 stained weakly to moderately in normal colorectal tissue, whereas 51% (22/43) of colorectal cancer tissues stained strongly for p53, correlating with advanced tumour stages (FIGS. 4 B and C). Anti-p53 antibodies were found to be present in 7 cancer patients strongly expressing the protein in the tumour tissue (Table 3) in accordance with previous studies. However, one patient positive for p53 antibody in serum exhibited no, staining for p53 in tissue.

TABLE 3

| Tissue p53 protein expression | | Serum p53 antibody |
| --- | --- | --- |
| No. of colorectal cancer patients | Staining intensity | No. of colorectal cancer patients |
| 5 | Negative | 1 |
| 16 | Weak-moderate | 0 |
| 22 | Strong | 7 |

TABLE 4

| Staining type: | Tumour tissue (n = 43) HMGB1 positive | Normal tissue (n = 38) HMGB1 positive | p-value |
| --- | --- | --- | --- |
| Nucleus | 40 (93%) | 34 (89%) | 0.7 |
| Cytoplasm | 29 (67%) | 2 (5%) | <0.0001 |

Sixty seven percent of tumours showed cytoplasmic staining for HMGB1. However, only 5% of the normal colorectal tissues showed cytoplasmic localisation (Table 4). All 19 non-cancer cases showed nuclear staining and 2 (11%) showed an additional cytoplasmic staining for HMGB1 (Table 5).

TABLE 5

| | Non-cancer controls (normal tissue) (n = 19) | |
| --- | --- | --- |
| Staining type: | HMGB1 Positive | HMGB1 Negative |
| Nucleus | 19 (100%) | — |
| Cytoplasm | 2 (11%) | 17 (89%) |

This significant difference (p<0.0001) indicates that cytoplasmic expression of HMGB1 occurs preferentially in malignant cells and may have implications in tumour pathogenesis.

To identify the potential of the antibody signature to detect cancer at an early stage, the 18 identified cancer markers were assessed in relation to the Dukes stages of corresponding patients. Of the 8 patients with serum antibody to p53, 1 patient was diagnosed Dukes A and 1 patient Dukes B, while 2 patients were Dukes C and 4 were Dukes D. This data shows that the presence of serum p53 antibodies correlates with advanced stage in colorectal cancer. While p53 antibodies correlates with advanced Dukes stage, the other 17 antigens do not show such a trend. For example, serum antibodies to SNP29 and ICLN are predominantly found in patients with earlier stages (Dukes A and B) while others such as CADM1 and HMGB1 show a uniform distribution over the different Dukes stages (data not shown). Therefore, this suggests that combination of such antigens may prove successful in detecting cancer at early and advanced stages of the disease.

Molecular Targets in Colorectal Cancer p53 and HER-2/neu are known to trigger antibody responses in cancer patients and are associated with tumour pathogenesis. HMGB1 has been implicated in the pathogenesis of colorectal cancer but there is a paucity of literature on the antibody profile in patients with colorectal cancer. FIG. 5 shows representative images of HMGB1 staining in tumour tissue. Nuclear staining for HMGB1 was identified in 93% of tumour tissues and in 89% of corresponding normal colorectal tissues (Table 4), is in agreement with earlier observations.

The invention is not limited to embodiments hereinbefore described which may be varied in construction and detail without departing from the spirit of the invention.

REFERENCES

1. Cho-Chung YS: Autoantibody biomarkers in the detection of cancer. Biochim Biophys Acta 2006, 1762:587-591.
2. J. M. Stewart and J. D. Young, Solid Phase Peptide Synthesis, 2nd edition, Pierce Chemical Company, Rockford, Ill. (1984), in M. Bodanzsky and A. Bodanzsky, The Practice of Peptide Synthesis, Springer Verlag, New York (1984)
3. Koehler and Milstein (Nature 256:495 [1975])
4. Sumerdon et al, (Nucl. Med. Biol 17:247-254 [1990]
5. Griffin et al, (J Clin One 9:631-640 [1991])
6. Lauffer, Magnetic Resonance in Medicine 22:339-342 [1991]).

The invention claimed is:

1. A method of identifying an individual suitable for colonoscopy, the method comprising a step of detecting in a biological sample taken from the individual presenting a symptom of colorectal cancer for the presence of a combination of autoantibodies against at least six biomarkers selected from SEQUENCE ID NOs: 1 to 12, the combination of autoantibodies being chosen such that detection of all the autoantibodies in the patient correlates to a greater than 50% risk of the patient being positive for colorectal cancer, wherein detection of all of the combination of the autoantibodies indicates that the patient should undergo a colonoscopy.

2. The method as claimed in claim 1 in which the combination of at least seven biomarkers.

3. The method as claimed in claim 1 in which the combination of all twelve biomarkers comprises the biomarkers of SEQUENCE ID NO's: 1 to 12.

4. The method as claimed in claim 1 comprising a step of assaying a biological sample from the individual for the presence of autoantibodies against at least six biomarkers of SEQUENCE ID No's 1 to 4, 7, 9 and 10, in combination with one, two, three or four proteins selected from the group comprising: SEQUENCE ID NO's 5, 6, 8, 11, and 12.

5. The method as claimed in claim 4 comprising a step of assaying a biological sample obtained from the individual for the presence of autoantibodies against at least six biomarkers of SEQUENCE ID No's 1 to 4, 7, 9 and 10.

6. The method as claimed in claim 5 comprising a step of assaying a biological sample obtained from the individual for the presence of autoantibodies against at least six biomarkers of SEQUENCE ID No's 1 to 4, 7, 9 and 10.

7. The method as claimed in claim 6 comprising a step of assaying a biological sample obtained from the individual for the presence of autoantibodies against seven of the proteins of SEQUENCE ID No's 1 to 4, 7, 9 and 10.

8. The method as claimed in claim 6 in which the positive biomarker is selected from the group consisting of SEQUENCE ID NO's 1 to 12.

9. The method as claimed in claim 1 in which the biological sample being assayed is serum.

* * * * *